US008652087B2

(12) United States Patent
Bellantone

(10) Patent No.: US 8,652,087 B2
(45) Date of Patent: Feb. 18, 2014

(54) METHOD FOR USE OF MICRODIALYSIS

(76) Inventor: Robert A. Bellantone, Yonkers, NY (US)

( * ) Notice: Subject to any disclaimer, the term of this patent is extended or adjusted under 35 U.S.C. 154(b) by 0 days.

(21) Appl. No.: 13/573,241

(22) Filed: Sep. 4, 2012

(65) Prior Publication Data

US 2013/0014562 A1    Jan. 17, 2013

Related U.S. Application Data

(62) Division of application No. 12/460,606, filed on Jul. 21, 2009, now Pat. No. 8,333,107.

(51) Int. Cl.
*A61M 1/16* (2006.01)
(52) U.S. Cl.
USPC .............................................. 604/28; 604/27
(58) Field of Classification Search
USPC ............................................ 604/27–29, 264
See application file for complete search history.

(56) References Cited

U.S. PATENT DOCUMENTS

| | | | |
|---|---|---|---|
| 6,346,090 B1* | 2/2002 | Liska et al. ..................... | 604/29 |
| 6,632,315 B2* | 10/2003 | Liska et al. ............... | 156/244.13 |
| 2001/0015253 A1* | 8/2001 | Liska et al. ............... | 156/244.13 |
| 2002/0123676 A1* | 9/2002 | Haueter et al. ................ | 600/309 |
| 2003/0220607 A1* | 11/2003 | Busby et al. .................... | 604/29 |
| 2003/0225067 A1* | 12/2003 | Stendel et al. ............. | 514/222.5 |
| 2005/0119588 A1* | 6/2005 | Model et al. .................. | 600/581 |
| 2009/0054854 A1* | 2/2009 | Hochmuth et al. ........... | 604/265 |
| 2009/0107907 A1* | 4/2009 | Chen et al. ............... | 210/321.71 |
| 2010/0113975 A1* | 5/2010 | Kuennecke et al. .......... | 600/573 |
| 2010/0204565 A1* | 8/2010 | Falken et al. ................. | 600/424 |

OTHER PUBLICATIONS

Kabir et al. Development of a pulsatile microdialysis method: Theory and application to the determination of drug diffusion coefficients, Ph.D. dissertation, Long Island University, The Brooklyn Center., Oct. 2003.*
Kabir et al., "Measuring Drug Concentrations Using Pulsatile Microdialysis: Theory and Method Development in vitro", International Journal of Pharmaceutics, No. 293 (2005), pp. 171-182.*
Siaghy et al., "Consequences of static and pulsatile pressure on transmembrane exchanges during in vitro microdialysis: implication for studies in cardiac physiology", Medical & Biological Engineering & Computing, vol. 37, No. 2, Mar. 1999, pp. 196-201.*

* cited by examiner

*Primary Examiner* — David A Rogers
(74) *Attorney, Agent, or Firm* — Jean B. Mauro

(57) ABSTRACT

Very accurate measurements of mass transfer can be made rapidly by permitting diffusion of an agent desired to be measured into or out of a small, very precisely known volume of a microdialysis probe, then rapidly pumping or flushing ("pulsing") the probe with a known volume of fluid as a single pulse. The diffusion and pulsing may be repeated. The method, hereinafter called pulsatile microdialysis (PMD) to distinguish it from prior art continuous flow microdialysis, is useful for measurements in a number of processes, including protein binding, adsorption to binding agents such as activated charcoal, release from microemulsion drug delivery systems, determination of drug diffusion coefficients and concentrations, and for various other purposes.
The method is based on mathematical manipulation of Fick's Laws. Resulting equations were verified against experimental data using methazolamide, warfarin and benzocaine as test drugs.

9 Claims, 13 Drawing Sheets

The fraction recovered ($F_R$) vs. exposure time.

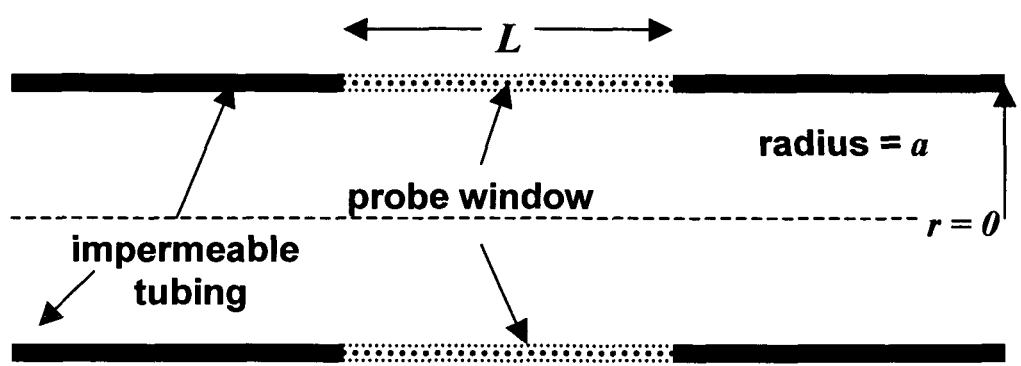
Figure 1. Schematic diagram of microdialysis probe. (Prior art)

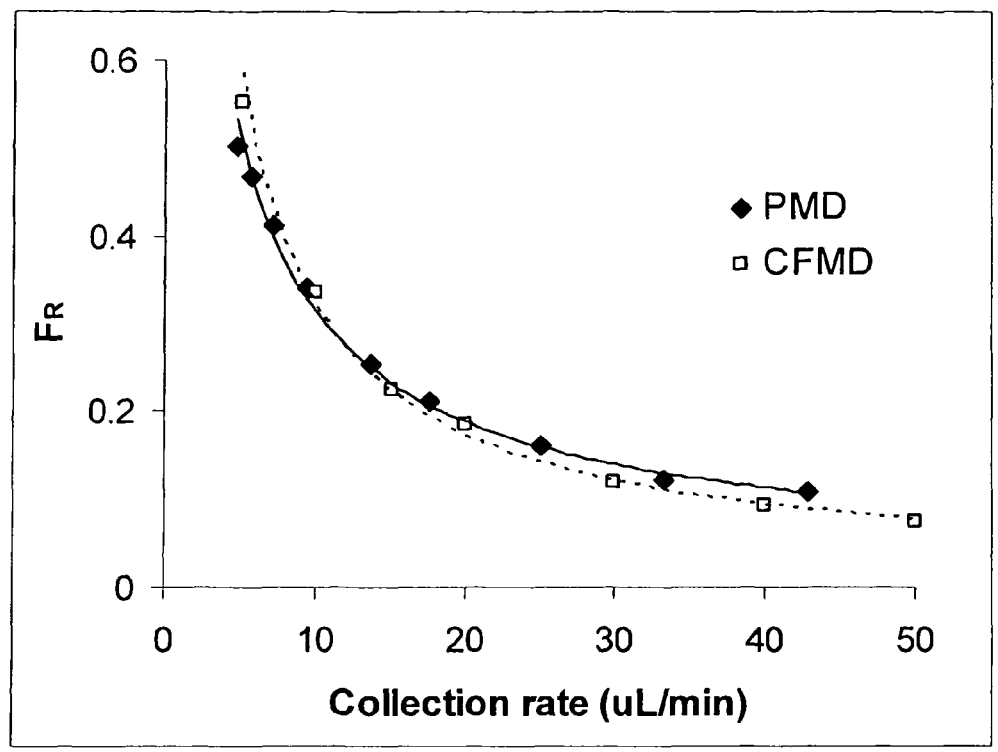
Figure 2. Comparison of $F_R$ for PMD and CFMD at sample collection rates.

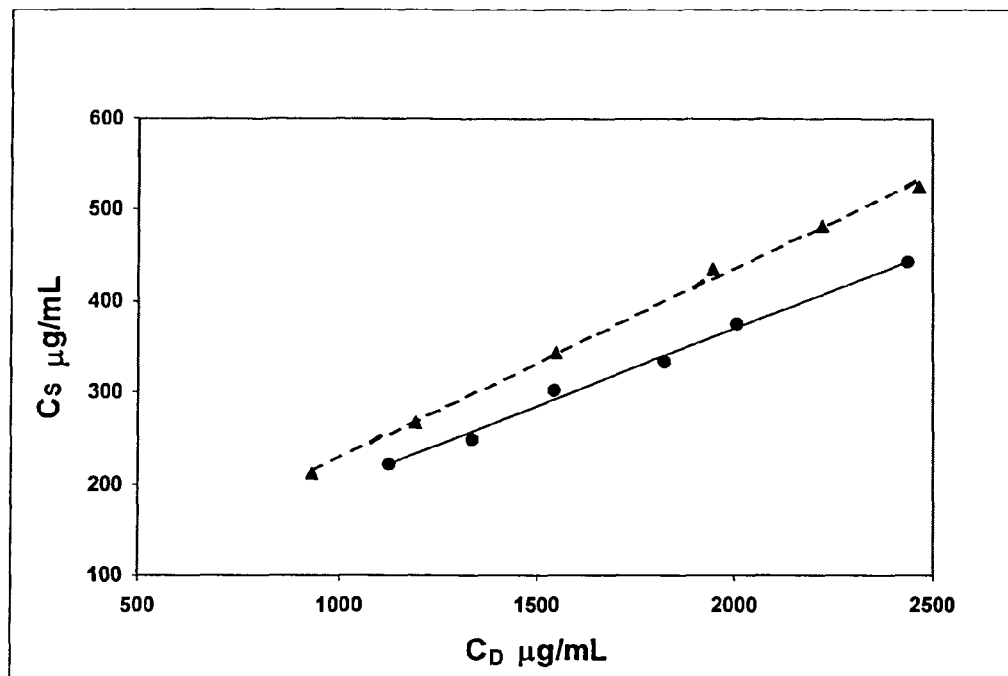
Figure 3. Donor-dialysate concentration calibration curves for two different probes.

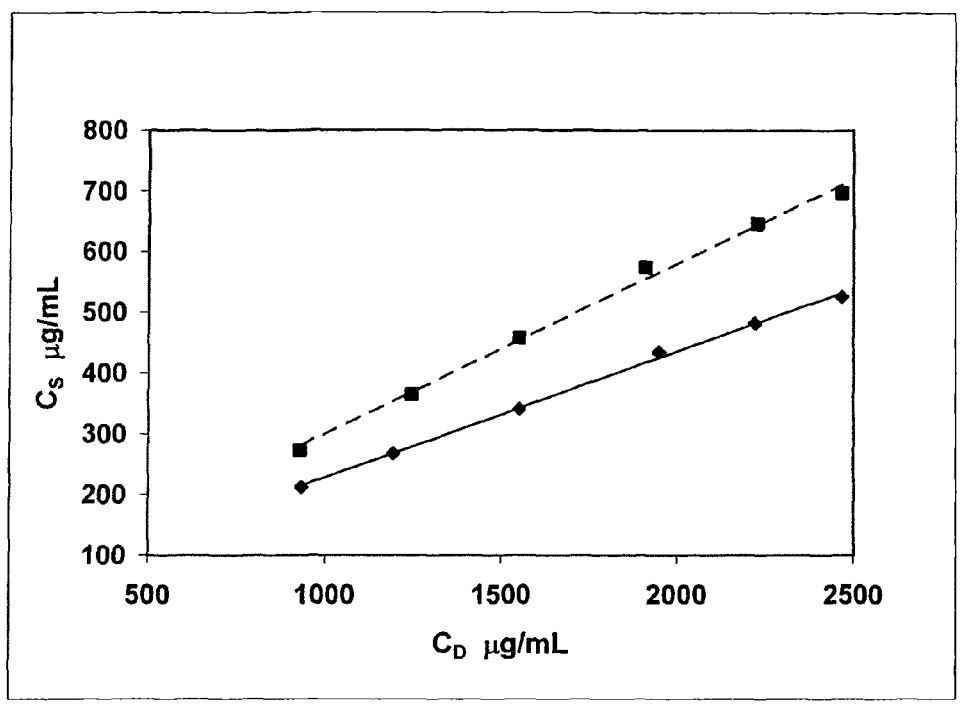
Figure 4. Donor-dialysate concentration calibration curves for two different resting times.

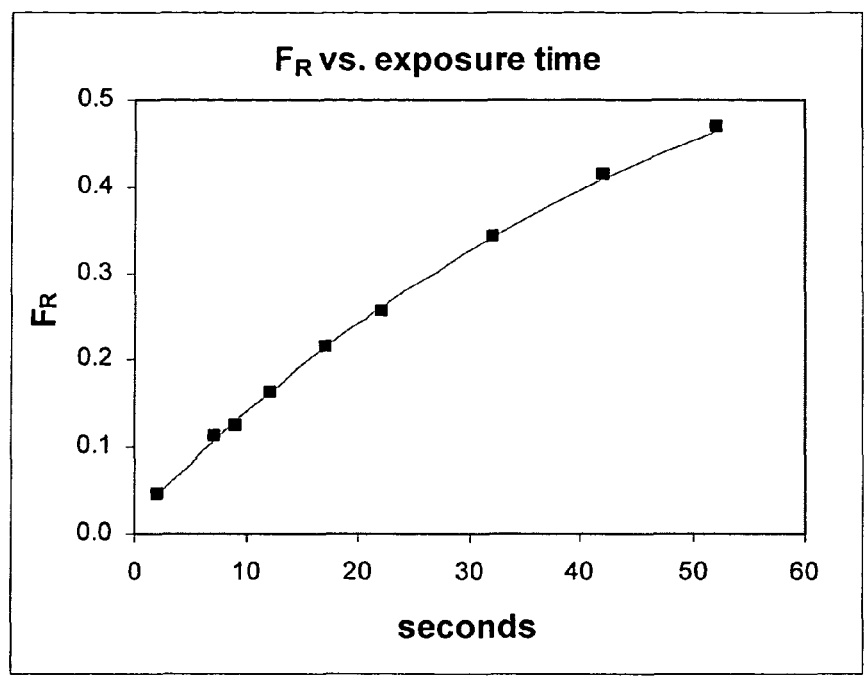
Figure 5. The fraction recovered ($F_R$) vs. exposure time.

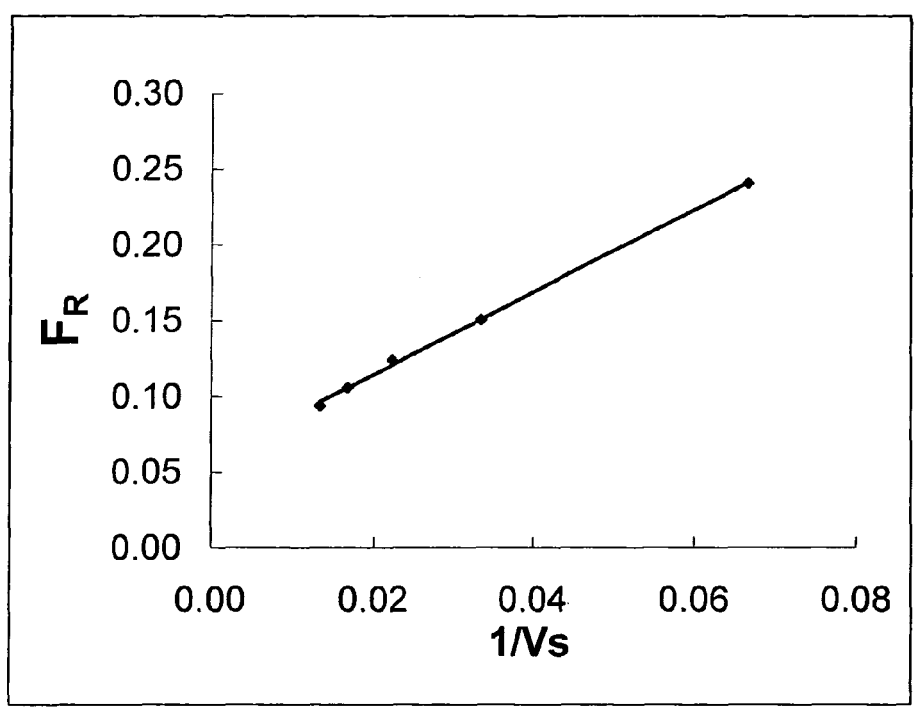
Figure 6. A plot of $F_R$ vs. $1/V_S$ using Equation (20).

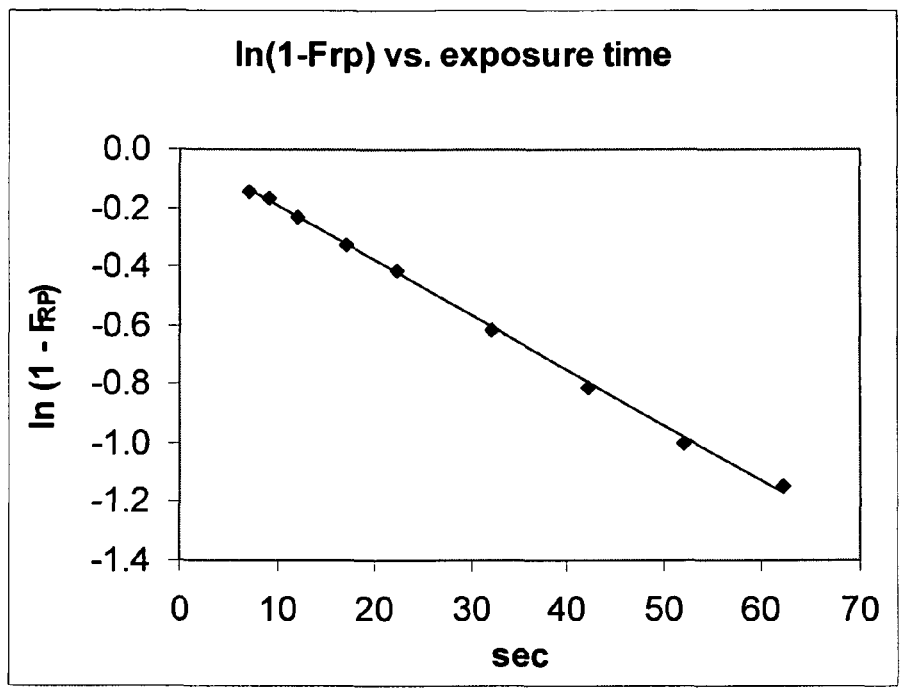
Figure 7. Log of (1 − $F_{RP}$) vs. exposure time. (Prior art)

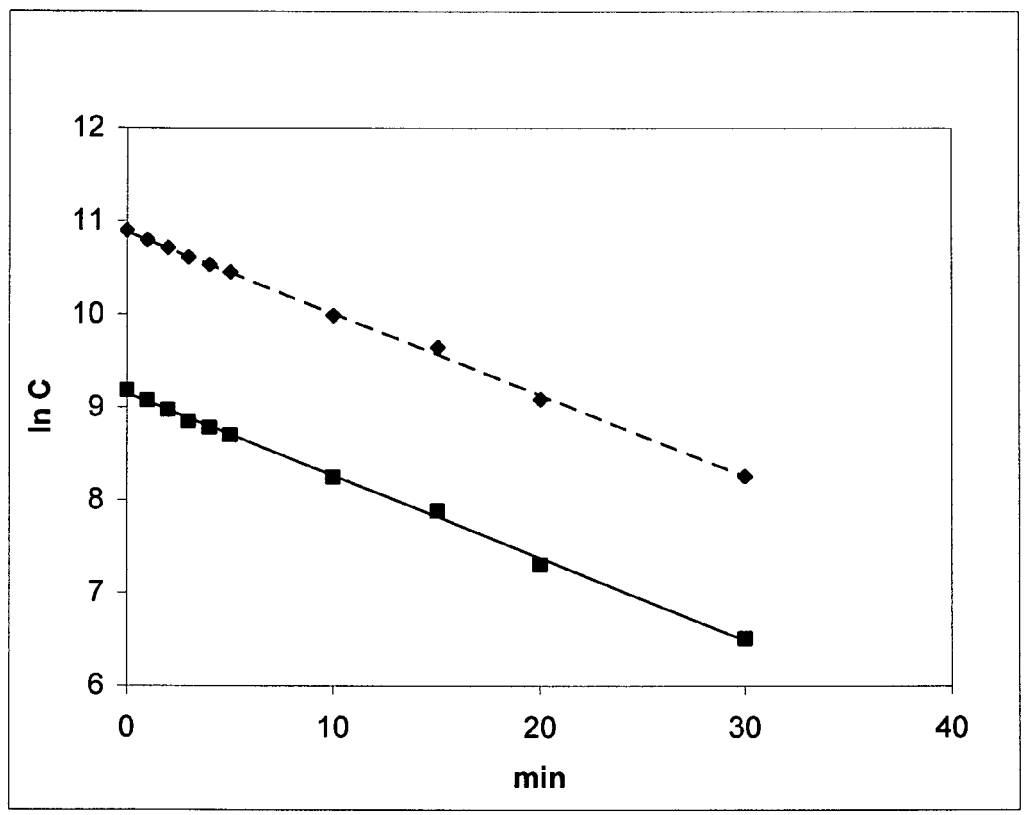
Figure 8. Log concentration vs. time for simulated first order drug uptake. (Prior art)

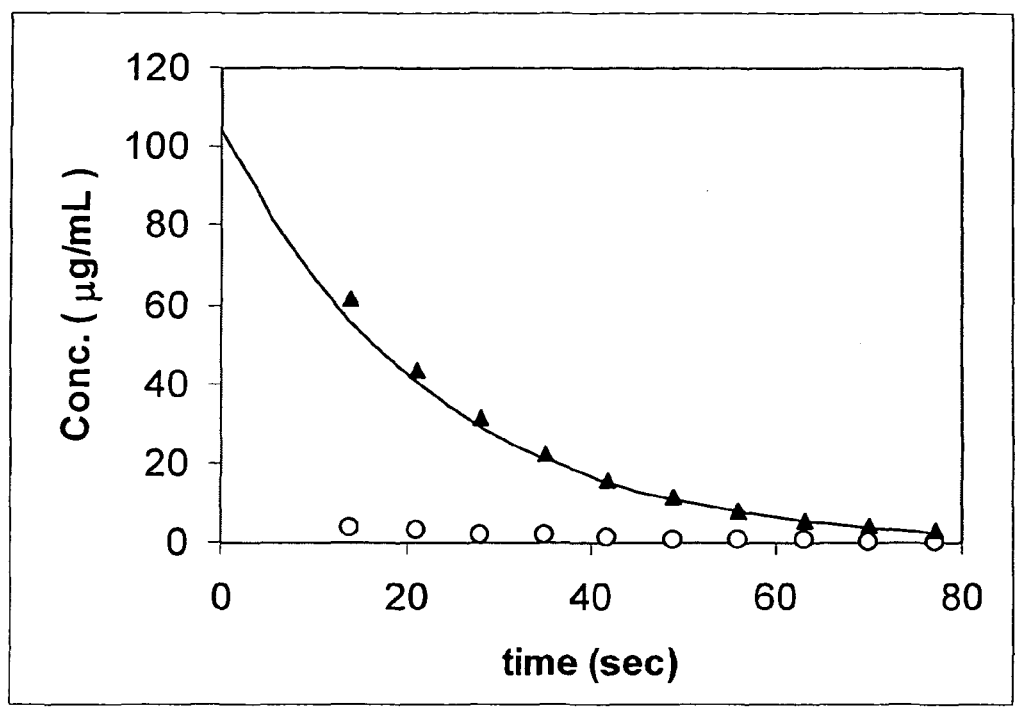
Figure 9. Rapid first order decline.

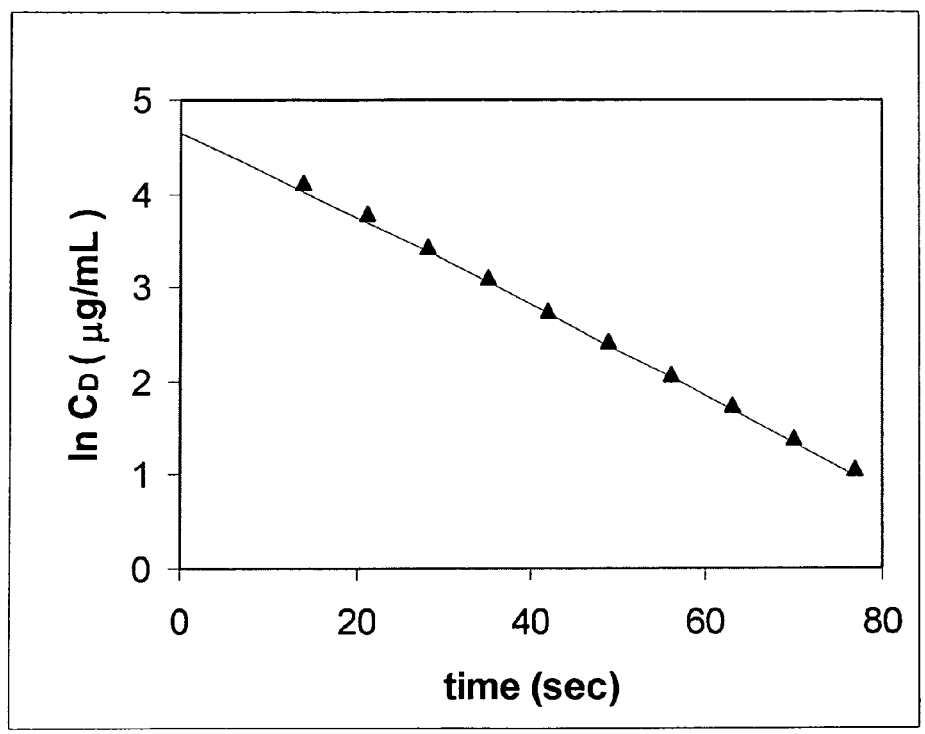
Figure 10. Rapid first order decline: log of the donor concentration vs. time

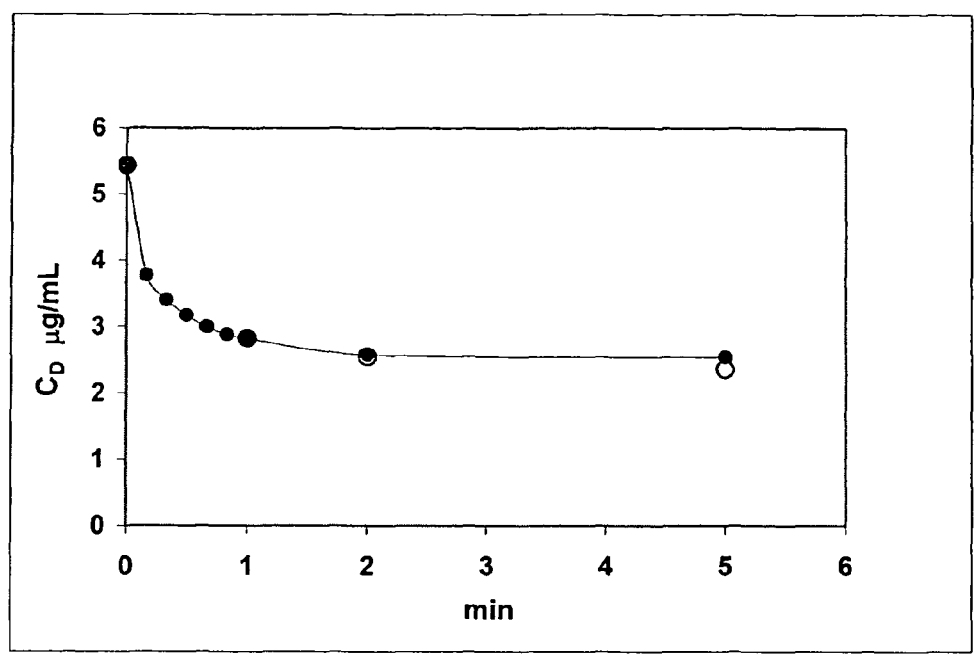
Figure 11. Comparison of PMD and donor direct sampling: concentration vs. time data for adsorption of MTZ by activated charcoal.

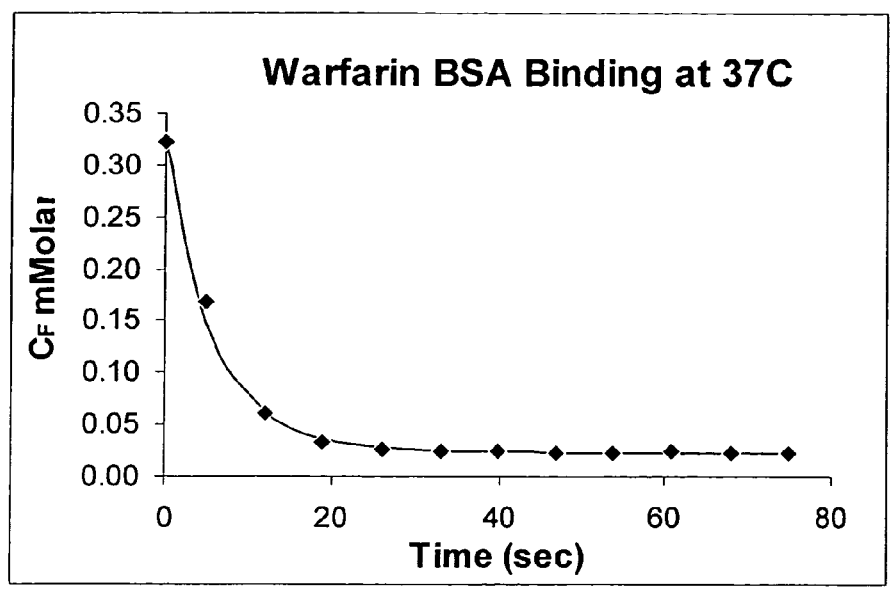
Figure 12. Binding of warfarin to bovine serum albumin at 37 °C.

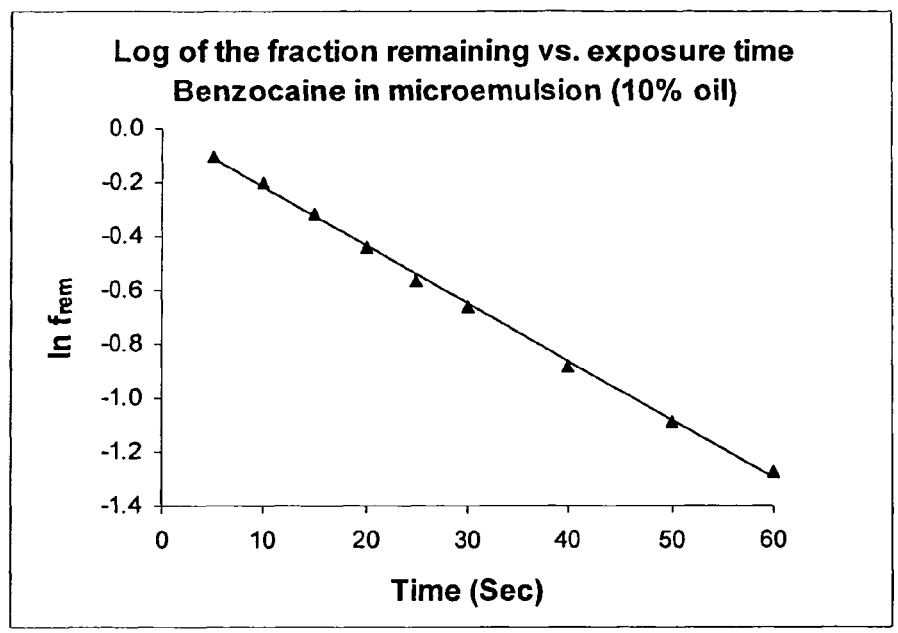
Figure 13. Release of benzocaine from Tween 20/Cremophor EL and peppermint oil microemulsions: log of the fraction remaining in the microemulsion vs. time.

METHOD FOR USE OF MICRODIALYSIS

BACKGROUND OF THE INVENTION

1. Field of the Invention

The invention relates to an improved method of effecting and measuring mass transfer. In particular, the invention relates to the use of an improved method of microdialysis for measuring the transfer of relatively small quantities of dissolved, suspended or otherwise dispersed material between two media (one inside and one outside the microdialysis probe). The transfer can be characterized by the loss of material from the medium in which it is contained and/or the collection by the other medium, and in particular can be used to sample drug concentrations and/or characterize the rates at which various processes occur and the extent of transfer. Examples include determination of drug solubility, and processes such as binding of drugs to proteins, chelation and complexation of drugs, adsorption of drugs in solution onto charcoal and other adsorbing agents, and release of drugs from emulsions and microemulsion systems. In addition, the rate of transfer can be used to determine the diffusion coefficients of drugs and permeabilities of coatings placed on the probe window. (Although these examples involve drugs and are of pharmaceutical interest, the invention extends to any chemical, particle or droplet that can transfer between two media by passing through a membrane). Other applications include determining drug dissolution rates, and precipitation/crystallization rates of a dissolved drug from supersaturated solutions. Other applications within the scope and intent of the invention will occur to those skilled in the art.

2. Summary of the Prior Art

Microdialysis performed in a continuous manner is a known method for sampling drug concentrations from media in biological tissues or in vitro systems; however, certain deficiencies, as will be discussed more fully below, have prevented its optimum application. The prior art technique is based on the dialysis principle, employing a "semipermeable" membrane, i.e., one that is highly permeable to water and small molecules. In this method, a sampling solution (dialysate) is perfused continuously through a probe, and a drug or other material of interest passively diffuses into the dialysate from the surrounding medium. The dialysate is collected and analyzed for drug content, and the concentration of drug or other material of interest in the surrounding medium is then estimated from that information. (An analogous procedure can be done in which the dialysate is the donor, and the amount of drug lost to the surrounding medium is determined. This is often referred to as retrodialysis or retromicrodialysis.)

Microdialysis can offer significant advantages compared to other sampling methods. For instance, since microdialysis probes are very small, they can be placed directly into biological tissue for in vivo testing or into small "receivers" for in vitro systems. In addition, the method offers the advantage of a clean aqueous sample without pre-detection sample preparation, such as separation or clean up steps. Consequently, microdialysis is becoming a standard technique for in vivo and in vitro analysis of drug and biochemical concentrations.

In the standard microdialysis method, dialysate is continuously perfused through the probe, usually at a constant flow rate. (This will be referred to as continuous flow microdialysis, or CFMD.) For purposes of this invention, the membrane will be referred to as highly permeable, i.e., it is permeable to water and relatively small molecules, particles and droplets (e.g., from a microemulsion) but impermeable to relatively large molecules such as proteins, etc. The essential parameter, of course, is that the membrane be permeable with respect to the material, e.g., a drug, that is to be measured or withdrawn by means of diffusion. The choice of perfusion flow rate for the dialysate is governed primarily by the sample size for the analysis. Typical CFMD perfusion flow rates range from 0.5 to 2.0 µL/min for samples that will be analyzed by high-pressure liquid chromatography (HPLC) methods, for example. At these flow rates, however, the time required for sampling is relatively long, and the time resolution of the samples (i.e., the ability to associate a specific concentration with a specific time or a short time interval) is poor. In addition, there are problems associated with generating sufficient sample volumes (5-20 µL) in short time intervals (less than 30 seconds, perhaps less than 5-10 seconds). For instance, the sample concentrations become very dilute and may fall below the detection limit of the assay being utilized. Consequently, CFMD is poorly suited for studies in which concentrations change relatively rapidly. Such cases arise frequently in pharmacy and biology, and can include in vitro cellular drug uptake kinetics studies or binding studies, drug complexation, drug adsorption to charcoal or other binding agents, precipitation from supersaturated solutions, etc. For example, it has been reported that methazolamide uptake by red blood cells suspended in buffer is very rapid at early times, with the buffer concentration decreasing by 50% in the first 1-2 minutes. For other systems, such as protein binding, a 50% decrease in concentration may occur in less than 10-15 seconds. For setups like these, the inability of CFMD to sample every 10-15 seconds is a great disadvantage. In addition, for sampling methods such as spiking, which requires separating the cells from the buffer, large errors can potentially occur because the uptake process continues during the sample preparation. Thus, a microdialysis method that can offer good time resolution within relatively short time frames would offer significant advantages for systems like these.

Another problem that can be associated with CFMD is that, at typical perfusion flow rates, the recovery of drug and the resulting sampling efficiency can be poor. The recovery of a drug is the relationship between concentrations of the drug in the donor fluid and that of the dialysate, and the fraction recovered ($F_R$) is defined in terms of the ratio of the dialysate concentration ($C_S$) and donor concentration ($C_D$). For dialysate initially void of drug, and when $C_D$ can be taken as constant, this is given as $$F_R = \frac{C_S}{C_D} \tag{1}$$

In vitro, a number of parameters influence the $F_R$, including the temperature, flow rate, probe length, and the physical properties of the drug, perfusate and membrane. Since the perfusion is continuous in CFMD, equilibrium between the dialysate and the donor medium is not approached, and the $F_R$ is typically low.

For retrodialysis, the analogous parameter would be the fraction remaining in the dialysate, $R_F$. Denoting the concentration in the dialysate before entering the probe as $C_0$, this is defined as $$R_F = \frac{C_S}{C_0} \tag{2}$$

For situations in which the concentration of the external medium changes appreciably during the time a microdialysis sample is taken, the $F_R$ defined above is not applicable because $C_D$ is changing with time. Thus, a method for determining the $C_D$ at specific times is needed. As discussed above, this is further complicated by the fact that taking samples rapidly is often difficult because processes can be ongoing during separation or other cleanup steps prior to sample assay. Thus, the need for a method to obtain specific values of $C_D$ at specific times using a fast method is apparent.

BRIEF DESCRIPTION OF THE DRAWINGS

FIG. 1 is a schematic diagram of a microdialysis probe.

FIG. 2 is a graph of the fraction of material recovered at various flow rates for pulsatile microdialysis vs. continuous flow microdialysis in which the donor is the medium outside the probe and does not change with time.

FIG. 3 shows calibration curves for two different probes for the case in which the donor medium is outside the probe and does not change with time.

FIG. 4 shows calibration curves for two different resting times for the same probe, for the case in which the donor medium is outside the probe and does not change with time.

FIG. 5 is a curve showing a measure of fraction recovered ($F_R$) as a function of the exposure time, in which the donor medium is outside the probe and does not change with time.

FIG. 6 is a curve showing a measure of In $(1-F_{RP})$ as a function of the exposure time.

FIG. 7 is a curve showing the fraction recovered ($F_R$) as a function of $1/V_S$.

FIG. 8 is a curve showing the log of the concentration as a function of time for first-order drug uptake for a case in which the drug concentration in the donor changes slowly and the donor is the medium outside the probe.

FIG. 9 is a curve showing the concentrations in the sample and donor as a function of time for a rapid first order decline in the drug concentration, in which the donor is outside the probe.

FIG. 10 is a curve showing the log of the concentration as a function of time for a rapid first order decline in the drug concentration, in which the donor is outside the probe.

FIG. 11 is a curve comparing the result of pulsatile microdialysis and direct donor sampling for the adsorption of methazolamide to activated charcoal.

FIG. 12 is a curve showing the free concentration of warfarin as a function of time in the presence of bovine serum albumin.

FIG. 13 is a curve showing the release of benzocaine from a microemulsion system as a function of time.

SUMMARY OF THE INVENTION

The invention comprises a method for transferring (withdrawing or donating) by diffusion at least some of a diffusible material (hereinafter variously called an agent or drug) contained (either dissolved or suspended) in a medium either inside or outside of a microdialysis probe.

In its broadest sense, the invention relates to pumping a dialysate in a pulsed manner and analyzing at least some of such dialysate for its content of a desired material. More specifically, the invention relates to a microdialysis process comprising pumping a dialysate through a probe, with an improvement comprising pumping the dialysate in a pulsed manner and analyzing at least some of such dialysate for its content of a desired material.

Still more specifically, the invention provides a method of performing microdialysis comprising:
a) providing a microdialysis probe comprising a section of relatively highly permeable membrane connected at its inlet to a source of dialysate and at its outlet to a receiver, and through which membrane a diffusible agent is to be transferred;
b) putting said probe in contact with said medium from which the at least some of said contained material is to be withdrawn, or to which some of the said material is to be donated, by diffusion;
c) perfusing a known quantity of a dialysate, which may or may not contain said agent, into the highly permeable section of the probe;
d) allowing said known quantity of dialysate to remain stationary for a period of time, called a resting time, sufficient to permit at least some of said contained material to diffuse into the dialysate from the external medium (acting as a donor medium), or to diffuse from the dialysate into the external medium (acting as a receiver medium);
e) flushing out ("pulsing") said known quantity of dialysate at a high flow rate with a single pulse of known volume of dialysate into a receiving container for subsequent analysis.

Because of the pulsing feature and the way it is applied in the present invention, which is believed to be unique to the present invention, the method is referred to herein as pulsatile microdialysis.

Pulsatile microdialysis has surprisingly been found to provide not only accurate but very rapid results, thus greatly facilitating, for instance, the ability to correlate in vitro with in vivo results in the case of drugs. Similarly, the methods of this invention have surprisingly been found applicable to determining a free drug concentration, as well as the concentration of the free form in the presence of other forms, including bound, precipitated, adsorbed, or complexed forms, or the presence of proteins, enzymes, and other large molecules, structures or particles. In addition, the present invention has surprisingly been found to be very useful for accurately determining the permeability of a porous device such as a microdialysis probe, and for accurately determining other properties of such a probe such as its window volume. Moreover, the instant invention provides surprisingly accurate measurement of diffusion coefficients, the rate of release of an agent dissolved in emulsion and/or microemulsion droplets, the rate of binding of a material under conditions of adsorption to particles, complexation, and chemical reaction.

For all the above uses, the present invention has been found to be extremely valuable for the accurate determination of changes in quickly changing systems.

In a preferred embodiment, the invention comprises the method described above wherein said probe comprises a tubular section of highly permeable membrane connected at each end to a section of relatively impermeable membrane or section of the probe.

In another preferred embodiment, the invention comprises a method as described above wherein said probe comprises a needle-type probe comprising a highly permeable tubular membrane concentrically positioned with a relatively impermeable tube. It will be understood by those skilled in the art that such terms as "highly" and "relatively," and the like, do not connote specific numerical values. They are to be interpreted in the context of the materials involved in both the construction of the probe and in the context of the materials (agents) desired to be diffused into the probe or left behind, as the case may be. For example, in the case of a highly diffusible agent, the "relatively" impermeable membrane may need to be essentially impermeable, e.g., glass. On the other hand, in the case of an agent of low diffusibility such as a large molecule or an agent bound to another material, the "relatively" impermeable area may have significant permeability to various substances but yet be sufficiently impermeable to the agent to be separated so as to be satisfactorily operable in the methods of the invention. Accordingly, the term "relatively" is intended to permit a reasonably broad choice of materials of construction for the probe.

In still another preferred embodiment, the invention comprises a method as described above wherein said probe comprises a well with an inlet and outlet that is separated from another well by a highly permeable membrane.

In yet another preferred embodiment, the invention comprises a method as described above wherein said probe, of either type mentioned in the previous two paragraphs, is directly connected to an apparatus for assay, such as direct connection to liquid chromatography equipment (HPLC).

As used herein, the term "probe" is intended to include any device of any geometry which is capable of being used in the methods described in the claims.

It will be readily understood by those skilled in the art that the terms "agent" and "drug" are often used interchangeably, and it will be further understood that the term "agent" is the broader term and is intended to include not only drugs but also any other pharmaceutically or chemically active material that will function in the present invention for any purpose for which the methods and mathematics of the present invention may be applied.

It will also be readily understood that while the instant invention is often described herein in connection with specific mathematical expressions, the spirit and advantages of the invention may also be possibly realized by application of other mathematical not disclosed herein but which do not avoid or limit the fundamental nature and scope of the invention.

DISCUSSION OF THE INVENTION

The approach taken by the instant invention to solving the problems associated with the conventional microdialysis method, referred to as continuous flow microdialysis (CFMD), is the use of a novel method of microdialysis, referred to as pulsatile microdialysis (PMD). In this method, the dialysate is pumped into the probe and then allowed to remain at rest for a brief, discrete period referred to as the resting time ($t_R$). After a suitable $t_R$ (typically 3-100 seconds, preferably 3-15 seconds), the dialysate is flushed (i.e., pumped) out and collected for assay. It is usually preferred that this flushing is done as a single pulse at a relatively high flow rate (typically 50-165 µL/min), preferably to minimize or eliminate the effects of further diffusion, which usually simplifies mathematical analysis of the data. The PMD method allows flexibility to optimize the experimental procedure. For instance, the $t_R$ can be chosen to be long enough to give an acceptable amount of transfer between the dialysate and external medium by diffusion, and short enough to provide the desired time resolution. In addition, the volume that is flushed (i.e., the sample volume) is chosen to completely collect the sample that was at rest in the probe window while minimizing its dilution. (For determining the concentration in the external medium, the time must be chosen long enough to allow enough of the drug to be collected by the dialysate, which is characterized by the fraction recovered $F_R$, which was defined by Equation (1). By analogy, when the dialysate is being used as the donor medium, the time must be long enough so some fraction of the drug in the dialysate is lost to the external medium, as given by Equation (2) for $R_F$). As a result, the PMD method offers two advantages over CFMD: First, the pulsatile method shows excellent time resolution, even for rapidly changing concentrations; second, the $F_R$ can be made higher with PMD by increasing the $t_R$, which can enable the detection of low concentrations of drug in the surrounding fluids using shorter time intervals than would be possible using CFMD.

GLOSSARY OF TERMS

| Term | Definition |
|---|---|
| a | inner radius of the microdialysis probe window. |
| A | area of the probe window = $2\pi aL$ |
| $\beta_n$ | roots of Equation (8) |
| CFMD | continuous flow microdialysis |
| $C_D$ | concentration in the donor solution |
| $C_0$ | concentration in dialysate before entering probe |
| $C_S$ | average concentration in a collected dialysate sample (=$M/V_S$) |
| D | diffusion coefficient of the drug in the dialysate |
| $\delta_n$ | defined by Equation (18) |
| $F_R$ | fractional recovery for a sample, defined by Equation (1) |
| $F_R^0$ | PMD concentration divided by concentration in donor at start of sample interval, defined by Equation (75) |
| $F_{RQ}$ | fractional recovery of the continuous portion of the PMD sample |
| $F_{RP}$ | fractional recovery of the pulsed portion of the PMD sample |
| $\gamma_n$ | defined by Equation (17) |
| h | thickness of the wall of the probe window (outer minus inner radius) |
| L | length of the microdialysis probe (=$V_W/\pi a^2$) |
| $\lambda$ | defined by Equation (9) |
| M | total amount of drug in the collected a dialysate sample |
| $M_Q$ | amount of drug in the sample portion that did not rest in the probe window |
| $M_P$ | amount of drug in the sample portion that rested in the probe window |
| P | permeability of the probe window |
| PMD | pulsatile microdialysis |
| Q | flow rate (µL/min) |
| $R_F$ | The fraction remaining in the dialysate (when the dialysate is the donor), defined by Equation (2) |
| $R_{FQ}$ | fraction remaining in the dialysate for the continuous portion of the PMD sample |
| $R_{FP}$ | fractional remaining in the dialysate for the pulsed portion of the PMD sample |
| $t_P$ | exposure time for the pulsed portion of the dialysate sample ($t_R + t_Q$) |
| $t_Q$ | transit time for the continuous portion of the dialysate sample = $V_W/Q$ |

-continued

GLOSSARY OF TERMS

| | |
|---|---|
| $t_R$ | resting time for dialysate in the probe window |
| $t_S$ | duration of sampling time interval = $V_S/Q$ |
| τ | tortuosity of pores in the probe window wall |
| $V_W$ | probe window volume = $\pi a^2 L$ (same as the volume of dialysate allowed to rest) |
| $V_S$ | volume of one dialysate sample |

Pulsatile Microdialysis: Mathematical Model for a Constant Concentration in the Medium Outside the Probe A prototype microdialysis setup is shown in FIG. 1, which illustrates a probe window made of a highly permeable tube of constant inner radius a, length L and volume $V_W$. In the most general case, microdialysis can be described in cylindrical coordinates as a transport of drug that occurs by a combination of passive diffusion in the radial direction, and convection plus passive diffusion in the axial direction. This is written mathematically as $$\frac{\partial C}{\partial t} = -v_z \frac{\partial C}{\partial z} + D \frac{\partial^2 C}{\partial z^2} + \frac{D}{r} \frac{\partial}{\partial r}\left(r \frac{\partial C}{\partial r}\right) \qquad (3)$$

Here, C is the concentration of the dialysate inside the probe at a given position and time, D is the diffusion coefficient of the drug in the dialysate, and $v_z$ is the axial velocity, which in general is a function of r but is typically (i.e., for CFMD) held constant with respect to time. On the right hand side of Equation (3), the first term represents the effects of convection, while the second and third terms represent the contribution the axial and radial diffusion, respectively. For the case of PMD, Equation (3) can be simplified as follows:
   While the dialysate is stationary in the probe, $v_z=0$ and the convection term can be ignored.
   The dialysate is moved into and out of the probe window quickly and completely. Thus, the exposure time (the time spent inside the probe window, and where diffusion can occur into or out of the probe) for any portion of the dialysate sample is well defined.
   The exposure time of the sample is chosen to be short enough to neglect axial diffusion. From the theory of separation of variables, for a tube of radius a, the relaxation time characteristic of the approach to equilibrium for diffusion in the radial direction is $\sim a^2/D$ (Carslaw and Jaeger, *Conduction of Heat in Solids*, Clarendon Press, Oxford, 1985). From random walk theory, the average distance traveled by diffusing molecules during a time interval t is $\sim\sqrt{Dt}$ (Reichl, *A Modern Course in Statistical Physics*, U. Texas Press, Austin, 1980, Chapter 6.). When the exposure time is comparable to the relaxation time, the average axial distance traveled due to diffusion is ~a. Since a<<L for microdialysis probes, axial diffusion will have a negligible effect on the mass balance in the sample.
   Even when the dialysate is being flushed, the exposure time for the flowing sample is short enough so the axial gradient does not have time to develop, and the $$v_z \frac{\partial C}{\partial z}$$

may be neglected.

As a result, Equation (3) reduces to $$\frac{\partial C}{\partial t} = \frac{D}{r}\frac{\partial}{\partial r}\left(r \frac{\partial C}{\partial r}\right) \qquad (4)$$

Equation (4) is a partial differential equation that requires one initial condition and two boundary conditions for its complete solution. The initial condition is that the dialysate is initially void of drug (or other material to be separated) when it enters the probe region of the microdialysis tube. The boundary conditions are, in part, obtained from the following considerations:
   The concentration in the medium outside the probe is constant (or may be approximated as constant) during each sampling period.
   The drug concentration is finite everywhere in the microdialysis probe.
   The dialysis tube wall is very thin and highly permeable, so pseudo-steady-state in the wall is established quickly. Thus, the flux of drug from the donor into the dialysate is proportional to the concentration difference across the wall of the probe window. The proportionality factor is the permeability P of the probe window, which is assumed to remain constant. The permeability is defined by the equation $$\frac{dM}{dt} = AP(C_D - C_R) \qquad (5)$$

where dM/dt is the rate at which the drug crosses the probe window wall, A is the area of the probe window, and $C_D - C_R$ is the concentration difference across the membrane (i.e., the difference in concentrations in the two liquid media at the inner and outer surfaces of the membrane).

Two cases will be considered below. The first is the case in which the donor is the medium outside the probe and the dialysate accumulates drug from the donor. The second is the case in which the dialysate is the donor and loses drug to the medium surrounding the probe.

The Donor Medium is Outside the Probe

When the medium outside the probe is the donor, then $C_D$ corresponds to the concentration outside the probe and $C_R$ is the concentration in the dialysate near r=a. For this case, the boundary and initial conditions are mathematically written as $$\begin{aligned} &\text{Initial condition} & C(r, 0) &= 0 & t &= 0 & (6) \\ &\text{Boundary conditions} & C(0, t) &= \text{finite} & r &= 0 \\ & & -D\frac{\partial C}{\partial r} &= P(C_D - C) & r &= a \end{aligned}$$

Using the separation of variables method, Equations (4) and (6) can be solved to give the concentration in a volume element of dialysate at a given radius as $$C(r, t) = C_D \left[ 1 - 2 \sum_{n=1}^{\infty} \frac{\lambda J_0(\beta_n r/a)}{(\beta_n^2 + \lambda^2) J_0(\beta_n)} \exp\left(-\frac{\beta_n^2 D t}{a^2}\right) \right] \quad (7)$$

Here, t is the length of time that a given volume element of dialysate was in the probe window (the exposure time), $J_0$ and $J_1$ are the zero-order and first-order Bessel function of the first kind, respectively (Carslaw and Jaeger, op. cit.; Ozisik, *Boundary Value Problems of Heat Conduction*, Dover Publications, New York, 1989), and the $\beta_n$ are the roots of the equation $$\beta_n J_1(\beta_n) - \lambda J_0(\beta_n) = 0 \quad (8)$$

where $$\lambda = \frac{aP}{D} \quad (9)$$

Values of $\beta_n$ have been tabulated for various values of $\lambda$ and n in the literature (Crank, *The Mathematics of Diffusion*, Clarendon Press, Oxford, 1975), and can also be calculated from Equation (8) using the nonlinear solvers included with spreadsheets such as EXCEL®. For the probes used here, it can be assumed that the drug does not partition into the probe material, and thus permeates the probe window wall exclusively through pores. If the donor and receiver media are similar, the partition coefficients between the pore medium and the donor or dialysate may be taken as unity. Thus, denoting the probe window porosity, thickness (difference between the outer and inner radii) and tortuosity by $\epsilon$, h and $\tau$, respectively, the permeability of the Window is given by $$P = \frac{\epsilon D}{\tau h} \quad (10)$$

which can be combined with Equation (9) to give $$\lambda = \frac{a\epsilon}{\tau h} \quad (11)$$

Thus, for these probes, $\lambda$ depends on properties of the probe window, but not properties of the drug or solvent. However, this is a special case of Equation (9). If the probes are coated or modified, then $\lambda$ depends not only on the geometrical properties of the probe, but also the material interactions between the drug and probe, and Equation (9) must be used.

The total amount of drug collected by the dialysate in the probe window after a given exposure time is found by integrating the concentration over the volume of the sample. Since the axial dependence is neglected in the mass balance, the mass in a sample of volume V with an exposure time t can be found from $$M = \frac{V}{\pi a^2} \int_0^a 2\pi r C(r, t) \, dr \quad (12)$$

Not all parts of a collected dialysate sample will be exposed to the donor for the same length of time, and two portions must be considered. One portion of the sample (referred to as the continuous portion) flows through the probe window without resting. The other portion (referred to as the pulsed portion) is pumped into the window, allowed to remain at rest for a resting time $t_R$, and then pumped out. For the continuous portion, the dialysate exposure time is simply the transit time $t_Q$ required for an element of fluid to move through the probe window. The exposure time $t_P$ for the pulsed portion is the sum of the resting and transit times. These are given, respectively, by $$t_Q = \frac{V_W}{Q} \text{ and } t_P = t_R + t_Q \quad (13)$$

where Q is the flow rate (volume per time) of the flushing. Thus, for a sample of volume $V_S$, the pulsed portion has a volume $V_W$ and accumulates a mass $M_P$ during a total exposure time of $t_P$, while the continuous portion has a volume $V_S - V_W$ and accumulates a mass $M_Q$ during an exposure time of $t_Q$. $M_P$ can be found by setting $t = t_P$ in Equation (7), performing the integration in Equation (12), and multiplying by the length of the probe window $V_W/\pi a^2$. $M_Q$ can be found by setting $t = t_Q$ in Equation (7), performing the integration in Equation (12), and multiplying by a length $(V_S - V_W)/\pi a^2$. The total mass of drug M in a collected sample is given by $$M = M_P + M_Q \quad (14)$$

where $$M_P = V_W C_D \left[ 1 - \sum_{n=1}^{\infty} \delta_n \exp(-\gamma_n t_P) \right] \quad (15)$$

$$M_Q = (V_S - V_W) C_D \left[ 1 - \sum_{n=1}^{\infty} \delta_n \exp(-\gamma_n t_Q) \right] \quad (16)$$

The constants $\gamma_n$ are $\delta_n$ are given by $$\gamma_n = \frac{\beta_n^2 D}{a^2} \quad (17)$$

$$\delta_n = \frac{4\lambda^2}{\beta_n^2 (\beta_n^2 + \lambda^2)} \quad (18)$$

where $$\sum_{n=1}^{\infty} \delta_n = 1 \quad (19)$$

(It should be noted that this form of $\gamma_n$ holds only for dialysate solutions. For two-phase systems, such as microemulsions, the form of $\gamma_n$ may change, but the use of $\gamma$ in the subsequent equations is expected to remain the same.)

When the concentration in the external medium is constant, or can be approximated as constant, the fractional recovery in the sample, defined in Equation (1), can be expressed in terms of the mass in the sample and the sample volume as $$F_R = M/V_S C_D M = V_S C_S \quad (20)$$

Similarly, the fractional recoveries of the pulsed ($F_{RP}$) and continuous ($F_{RQ}$) portions of the sample are defined as $$F_{RP} = \frac{M_P}{V_W C_D} = 1 - \sum_{n=1}^{\infty} \delta_n \exp(-\gamma_n t_P) \quad (21)$$

$$F_{RQ} = \frac{M_Q}{(V_S - V_W) C_D} = 1 - \sum_{n=1}^{\infty} \delta_n \exp(-\gamma_n t_Q) \quad (22)$$

The total mass in the sample can be written as $$M = V_W C_D F_{RP} + (V_S - V_W) C_D F_{RQ} \quad (23)$$

Since M is proportional to the donor concentration $C_D$, linear calibration plots relating $C_D$ and $C_S$ can be constructed according to Equation (1). It is also possible to rewrite Equation (23), as $$F_R = \frac{V_W}{V_S}(F_{RP} - F_{RQ}) + F_{RQ} \quad (24)$$

For a constant flow rate, $F_{RQ}$ corresponds to the fractional recovery for CFMD, as can be seen from Equations (21), (22) and (24) when $t_R = t_Q$ (equivalently, $t_R = 0$). This provides a procedure for obtaining the $F_{RQ}$ from $F_R$ data according to the condition that $$F_{RQ} = \lim_{t_R \to 0} F_R \quad (25)$$

This can be done in practice by fitting the $F_R$ vs. $t_R$ to an empirical function using nonlinear regression, and then taking the value of the function for $t_R = 0$. Since the above theory predicts that $F_R$ varies exponentially with the exposure time, this is using the equations below:

$$F_R = a_1 \exp(-b_1 t_R) + a_2 \exp(-b_2 t_R) + a_3 \quad (26)$$

$$F_{RQ} = a_1 + a_2 + a_3 \quad (27)$$

Since $F_R$ and $F_{RQ}$ can be determined experimentally (see Equation (1) and Example 1, respectively), it is possible to obtain $F_{RP}$ for any exposure time $t_P$ from Equation (24). However, this requires accurately knowing the window volume $V_W$. In practice, when a probe is first used, it is calibrated to determine $V_W$, which then allows the $F_{RP}$ to be calculated in any subsequent experiment using that probe. (It should be noted that simply calculated $V_W$ using manufacturer's specifications or optical measurements is not accurate enough for many of the analyses presented here. Thus, it is preferred to measure $V_W$ by plotting $F_R$ vs. $1/V_S$, using a constant resting time with a known value of $F_{RP}$. This discussed more fully below.)

The approach to equilibrium is characterized in the above equations by the exponential transient terms in the infinite series. For all values of λ and n, both the $\delta_n$ and exponential terms are between zero and one, and both tend toward zero with increasing n or time of exposure. Using typical values for the dialysis probes used in this study (a~100-150μ, h=8-12μ, ε<0.05) and a typical tortuosity value (τ>1.5-2), Equation (11) shows that 0<λ<0.5. For this range of λ, numerical calculations show that $\delta_1 > 0.99$ and $\delta_2/\delta_1 < 0.005$. Thus, there is negligible error (less than 0.1-0.5%) introduced by neglecting the n>1 terms, so Equations (21) and (22) can be written as $$F_{RP} = \frac{M_P}{V_W C_D} = 1 - \delta_1 \exp(-\gamma_1 t_P) \quad (28)$$

$$F_{RQ} = \frac{M_Q}{(V_S - V_W) C_D} = 1 - \delta_1 \exp(-\gamma_1 t_Q) \quad (29)$$

$$\ln(1 - F_{RP}) = \ln \delta_1 - \gamma_1 t_P \quad (30)$$

where $$\gamma_1 = \frac{\beta_1^2 D}{a^2} = \frac{\pi L \beta_1^2 D}{V_W} \quad (31)$$

$$\delta_1 = \frac{4\lambda^2}{\beta_1^2 (\beta_1^2 + \lambda^2)} \quad (32)$$

where $$\beta_1 J_1(\beta_1) - \lambda J_0(\beta_1) = 0 \quad (33)$$

and $F_{RP}$ is determined from Equation (24).

In theory, plots of $\ln(1 - F_{RP})$ vs. $t_P$ can be used to determine $\gamma_1$ and $\delta_1$ (which, in turn, can be used in Equations (8) and (18) to find λ). This is true for finding $\gamma_1$ because small experimental errors will minimally affect the slope. However, the intercept is typically close to zero because $\delta_1$ is close to 1, so experimental errors can result in significant relative errors in the intercept. Because small errors in the value of $\delta_1$ can result in relatively large errors in the corresponding λ, the approximations are made that $$\delta_1 = 1 \text{ neglect } n > 1 \text{ terms} \quad (34)$$

$$F_{RP} = 1 - \exp(-\gamma_1 t_P) \quad (35)$$

$$F_{RP} = 1 - \exp(-\gamma_1 t_Q) \quad (36)$$

Since $\delta_1$ is taken as 1, only $\gamma_1$ is obtained from a plot of Equation (35). However, to accurately find the $F_{RP}$ and avoid possibly substantial errors in value of $\gamma_1$, it is necessary that the window volume $V_W$ be accurately known. (Methods to determine $V_W$ are presented below.) It is also possible to obtain $\gamma_1$ using an alternative method, which is given by Equation (47) below.

The probe window wall permeability coefficient can be calculated using PMD as well. From Equations (13), (28) and (34), the mass in the pulsed portion of the sample is given by $$M_P = V_W C_D F_{RP} = V_W C_D [1 - \exp(-\gamma_1 t_Q) \exp(-\gamma_1 t_R)]$$

Using Equation (14) and noting that $M_Q$ is constant when all samples are taken in the same manner, the rate of uptake of the drug into the dialysate is given by $$\frac{dM}{dt} = \frac{dM}{dt_R} = V_W C_D \gamma_1 \exp(-\gamma_1 t_Q) \exp(-\gamma_1 t_R)$$

Using Equation (29) gives $$\frac{dM}{dt} = V_W C_D \gamma_1 (1 - F_{RQ}) \exp(-\gamma_1 t_R)$$

If $t_R=0$, this can be written as $$\frac{dM}{dt} = V_M C_D \gamma_1 (1 - F_{RQ}) \quad (37)$$

At very early times ($t_R$ approaching zero), the receiver concentration $C_R$ (here, corresponding to the dialysate concentration near the probe membrane) is negligible compared to the donor concentration $C_D$ (corresponding here to the concentration in the external solution), and Equation (5) can be simplified to $$\frac{dM}{dt} = APC_D \quad (38)$$

Here, A is the area of the probe window, which can be obtained from $V_W$ and the length of the Window L (which is easily measured). Combining Equations (37) and (38) leads to $$P = \frac{V_W \gamma_1 (1 - F_{RQ})}{A}$$

A refinement can be done as follows. The value of dM/dt in the limit of $t_P=0$ can be obtained graphically from a plot of M vs. $t_R$ by doing a best fit of the curve and extrapolating to $t_R=-t_Q$. This would correspond to $F_{RQ}=0$ and $C_R=0$. Thus, Equation (38) would hold exactly and the Equation (37) would be written as $$\frac{dM}{dt} = V_W C_D \gamma_1 \quad (39)$$

As a result, the permeability would be given as $$P = \frac{V_W \gamma_1}{A} \quad (40)$$

From the above, it is possible to obtain the diffusion coefficient D of a drug in the dialysate medium. Equations (8), (9) and (17) lead to $$\lambda = \frac{\beta_1 J_1(\beta_1)}{J_0(\beta_1)} \quad (41)$$

$$\gamma_1 = \frac{\beta_1^2 D}{a^2} \quad (42)$$

$$\frac{P}{\gamma_1 a} = \frac{J_1(\beta_1)}{\beta_1 J_0(\beta_1)} \quad (43)$$

Knowing P, a and $\gamma_1$ allows $\beta_1$ to be calculated from Equation (43), which then allows D to be calculated from Equation (42) and $\lambda$ from Equation (9) or Equation (41).

As mentioned above, the volume of the probe window must be accurately known to obtain accurate values of the $F_{RP}$. Since optical measurements and using manufacturers' nominal specifications are not accurate enough, the methods presented here were developed to more accurately determine $V_W$.

If a long resting time is used in a PMD experiment, then the concentrations of the dialysate resting in the probe window and in the medium outside the probe will equilibrate, so $$F_{RP} \to 1 \text{ long } t_R \quad (44)$$

and Equation (24) becomes $$F_R = F_{RQ} + V_W (1 - F_{RQ}) \frac{1}{V_S} \quad (45)$$

A plot of $F_R$ vs. $1/V_S$ will give an intercept of $F_{RQ}$ and a slope of $V_W(1-F_{RQ})$, which will allow the calculation of $V_W$. ($F_{RQ}$ can also be measured independently from CFMD data.) A variation of this method that will not require long resting times is to obtain a matrix of $F_R$ vs. $1/V_S$ for a range of resting times, and perform a nonlinear regression on the matrix. However, the preferred method of using Equation (45) is preferred because it avoids the potential numerical problems associated with nonlinear regressions.

Another variation that would also avoid the need for long resting times is as follows. If all samples are taken in the same way, $V_S$ and $F_{RQ}$ are constant, and $V_W$ does not change. Thus, rewriting Equation (24) as $$F_R = \frac{V_W}{V_S} F_{RP} + \text{constant}$$

and taking the derivative gives $$\frac{dF_R}{dt_R} = \frac{V_W}{V_S} \frac{dF_{RP}}{dt_R} \quad (46)$$

Combining this with Equation (28) and approximating $\delta_1=1$, which is valid for microdialysis probes, gives $$\frac{dF_R}{dt_R} = \frac{V_W \gamma_1}{V_S} \exp(-\gamma_1 t_Q) \exp(-\gamma_1 t_R)$$

This derivative is always positive, and taking the natural log gives $$\ln\left(\frac{dF_R}{dt_R}\right) = -\gamma_1 t_R + k' \quad (47)$$

$$k' = -\gamma_1 t_Q + \ln\left(\frac{V_W \gamma_1}{V_S}\right) \quad (48)$$

where k' is a constant. From a plot of the natural log of the derivative vs. the resting time in Equation (47), $\gamma_1$ is obtained from the slope and $V_W$ can be obtained from the intercept. It should be noted, however, that this method gives good results for $\gamma_1$ but is not as good for obtaining $V_W$. In practice, $V_W$ is best obtained from Equation (24) by plotting $F_R$ vs. $1/V_S$ (described in Example 1 below). This can be then be used when obtaining $\gamma_1$ by taking the slope of Equation (47), subject to the constraint that the intercept k' be consistent with the value of $V_W$ obtained from the plot of Equation (24). This is easily done in Microsoft Excel® (using the Solver function) and other programs.

It should be noted that Equation (47) provides an alternative method for determining the parameter $\gamma_1$ from the slope of the log $(dF_R/dt_R)$ vs. $t_R$ or $t_P$ (since $t_P = t_R + t_Q$ leads to $dt_P = dt_R$ when $t_Q$ is constant). In practice, this method works well. It is typically done by fitting the $F_R$ vs. $t_R$ data to an empirical function (usually bi-exponential plus a constant), taking the derivative analytically, and then plotting the log of the derivative vs. $t_R$.

From the above, it is possible to use PMD to characterize the volume of the probe window, its permeability coefficient for any drug, and the parameter $\lambda$. Some example methods are described below.

The Donor Medium is Inside the Probe (Dialysate)

When the donor is inside the probe, $C_D$ corresponds to the concentration in the dialysate near the probe wall ($r=a$) and $C_R$ is the concentration in the medium outside the probe. If the receiver concentration is always close to zero (sink conditions), and if the concentration of drug (or other material to be separated) in the dialysate before entering the probe is denoted by $C_0$, then the boundary and initial conditions that must be used in solving Equation (4) are given as $$IC: \quad C(r,0) = C_0 \quad t = 0 \tag{49}$$
$$BC: \quad -D\frac{\partial C}{\partial r} = PC \quad r = a$$
$$C(0, t) = \text{finite} \quad r = 0$$

Using the separation of variables method, Equations (4) and (49) can be solved to give the concentration in a volume element of dialysate at a given radius and time as $$C(r, t) = 2C_0 \sum \frac{\lambda J_0(\beta_n r/a)}{(\beta_n^2 + \lambda^2) J_0(\beta_n)} \exp\left(-\frac{\beta_n^2 D t}{a^2}\right) \tag{50}$$

where the symbols have the same definitions as those given previously. The same considerations outlined above hold, so the approximation of Equation (34) leads to $$C(r, t) = \frac{2C_0 \lambda J_0(\beta_1 r/a)}{(\beta_1^2 + \lambda^2) J_0(\beta_1)} \exp(-\gamma_1 t)$$

Following steps analogous to those presented above (for the donor outside the probe setup) leads to a set of equations analogous to the ones given for that case. In this case, the quantity of interest is the mass of drug that is left in the dialysis sample, which is given by $M = M_P + M_Q$, where $$M_P = V_W C_0 \exp(-\gamma_1 t_P)$$

$$M_Q = (V_S - V_W) C_0 \exp(-\gamma_1 t_Q)$$

It is useful to define the fraction of drug remaining in the dialysate sample by the term $R_F$, given by Equation (2), which is analogous to the $F_R$ term discussed in the previous section. It is also possible to define the fraction remaining from the pulsed and continuous portions, $R_{FP}$ and $R_{FQ}$, respectively, as $$R_{FP} = \frac{M_P}{V_W C_0} = \exp(-\gamma_1 t_P) \tag{51}$$

$$R_{FQ} = \frac{M_P}{(V_S - V_W) C_0} = \exp(-\gamma_1 t_Q) \tag{52}$$

which leads to $$R_F = \frac{V_W}{V_S} R_{FP} + \frac{V_S - V_W}{V_S} R_{FQ} \tag{53}$$

It is possible to find the $R_{FQ}$ in a manner analogous to given in Equations (26) and (27) by fitting the $R_F$ vs. $t_R$ data to an empirical function using nonlinear regression, and then taking the value of the function for $t_R=0$, using the equations below:

$$R_F = 1 - a_1 \exp(-b_1 t_R) - a_2 \exp(-b_2 t_R) \tag{54}$$

$$R_{FQ} = 1 - a_1 - a_2 \tag{55}$$

Following a mathematical analysis that is similar to that leading to Equations (30) and (47) leads to the following equations that can be used to obtain $\gamma_1$:

$$\ln R_{FP} = -\gamma_1 t_P \tag{56}$$

$$\ln\left|\frac{dR_F}{dt_r}\right| = -\gamma_1 t_R + \ln\left(\frac{\gamma_1 V_W}{V_S}\right) - \gamma_1 t_Q \tag{57}$$

It should be noted that $R_F$ decreases with increasing $t_R$, so the log is taken of the absolute value of the derivative. (This is reflected in the right hand side of Equation (57) as well.) Equations for the permeability of the probe wall, and thus $\lambda$, can be found as follows. Following logic analogous to that presented for the donor in the medium outside the probe, if the receiver concentration is constant and can be approximated as zero, then the initial rate of loss from the dialysate (at $t_P$ approaching zero, which is equivalent to $t_R = -t_Q$), is $$\frac{dM}{dt_R} = -APC_0 \tag{58}$$

where the (−) sign signifies that the drug is lost from the dialysate. From Equations (51) and (53), $$\frac{dM}{dt_R} = C_0 \frac{V_W}{V_S} \frac{dR_{FP}}{dt_R}.$$

which leads to $$\frac{dM}{dt_R} = -V_W C_0 \gamma_1 \exp(-\gamma_1 t_Q) \exp(-\gamma_1 t_R)$$

When $t_R = -t_Q$, this gives $$\frac{dM}{dt_R} = -V_W C_0 \gamma_1 \tag{59}$$

Combining Equations (58) and (59) gives the permeability as $$P = \frac{V_W \gamma_1}{A} \quad (60)$$

which is the same as Equation (40).

Pulsatile Microdialysis: Mathematical Model when the Donor Medium is Outside the Probe and the Donor Concentration is Rapidly Changing It is sometimes of interest to measure concentrations in the medium outside the probe for cases in which the concentration of free drug changes rapidly. This can occur with protein binding and other processes. One problem associated with such rapidly changing systems is obtaining samples often enough to characterize the donor concentration over time. However, if the concentration in the medium outside the probe (which will be considered as the donor here) changes significantly during the collection of a PMD sample, then it becomes necessary to determine both a donor concentration and the time at which the donor had that concentration. The concentration in a PMD sample is a reflection of the mass taken up during the entire sampling interval and does not give specific details about the rate of mass accumulation at any specific time in the interval. Thus, an extension of the analysis in the previous section (for constant external medium concentration) is needed to find a specific donor concentration that occurs at a specific time. This is not a problem when the donor concentration changes very slowly or is static, but must be addressed for the fast systems mentioned above.

In practice, each PMD sample is a combination of three portions or sub-samples—one that is initially pumped through the probe window without resting, followed by one that is pumped into the probe window and then allowed to remain at rest for a given time (known as the resting time $t_R$), and a final portion that is used to flush the probe window without resting. Sub-samples are categorized according to the exposure time of the dialysate (i.e., time spent in the probe window). Within each sub-sample, all small volume elements of fluid are exposed to the donor for the same time $\Delta t$, but $\Delta t$ will not be the same for any two consecutive sub-samples. This is important because the exposure time will affect how much drug is accumulated in the dialysate. In addition, not all parts of the dialysate enter the probe window at the same time, which must be considered when the donor concentration changes with time.

Below, the mass taken up by a PMD sample will be calculated in terms of the free donor concentration (dissolved and not bound or adsorbed) and relevant PMD parameters. This will be done for an arbitrary PMD sub-sample by calculating the rate of drug accumulation in an infinitesimal volume element of dialysate, integrating over the entire exposure interval to find the mass accumulated by the element while in the probe window, and then summing the masses for all elements to find the total mass in the sub-sample. Subsequently, this analysis will be applied to each PMD sub-sample and the mass accumulated in a complete PMD sample will be found. Two cases will then be considered—when the donor concentration (free drug) is constant (static donor), and when the donor concentration changes with time (dynamic donor).

The Mass Accumulated in a PMD Sub-sample

For a constant donor concentration $C_D$, the mass of drug in a PMD sub-sample is given by Equation (15) or (16). Using the Equation (34) and denoting the exposure time in the sub-sample (either $t_Q$ or $t_P$) by $\Delta t$, the concentration of drug in the PMD sub-sample is given by $$C = C_D(1 - \exp[-\gamma_1 \Delta t]) \quad (61)$$

Here, as before, $\gamma$ characterizes how quickly the concentration in the dialysate approaches equilibration with the donor and can be determined experimentally (discussed below).

If the concentration in the donor is not constant, then Equation (61) no longer holds because different parts of the sample enter the probe window at different times, and are thus exposed to different donor concentrations. Instead, the instantaneous rate of accumulation must be considered. Here, we will consider an infinitesimal volume element of dialysate that enters the probe window between times $t'$ and $t'+dt'$, has a infinitesimal volume $dV=Qdt'$, and has been within the probe window for a time $t_E$ ($0 \leq t_E \leq \Delta t$). While the given volume element is in the probe window, the donor concentration is a function of the time when the element is in the probe, given as $t=t'+t_E$. Thus, the rate of change of concentration in that volume element is $$\frac{dC}{dt} = \gamma_1 C_D(t', t_E) \exp[-\gamma_1 t_E]$$

and the mass of drug in the volume element (denoted by $m=C\,dV$) accumulates at a rate $$\frac{dm}{dt} = \frac{dC}{dt} dV = \gamma_1 C_D(t', t_E) \exp(-\gamma_1 t_E) Q dt' \quad (62)$$

The mass accumulated in the volume element while it is in the probe window is found by integrating Equation (62) over the exposure interval $t_E=0$ to $\Delta t$, or $$m = dt' \int_0^{\Delta t} \frac{dm}{dt} dt_E$$

The total mass in the sample is found by adding the mass accumulated in all the volume elements, which is done by integrating over all entry times to give $$M = \int_{t_0}^{t_f} m\, dt' = \int_{t_0}^{t_f} dt' \int_0^{\Delta t} \frac{dm}{dt} dt_E \quad (63)$$

where $t_0$ and $t_f$ denote the entry time into the probe window for the first and last volume elements of the sub-sample, respectively.

Application to a Complete PMD Sample

As mentioned above, a complete PMD sample is a combination three sub-samples, each with its own exposure time $\Delta t$. In general, the exposure time $\Delta t = t_Q + t_R$, where $t_R$ is the chosen resting time and $t_Q$ is the transit time given by Equation (13). In addition, not all parts of the PMD sample enter the probe window at the same time, so different parts of each sample and sub-sample are in the probe window at different times and are therefore exposed to different donor concentrations. In what follows, the start time for the PMD sample will be denoted as $t^0$, which will be taken as the time when the flushing of the previous sample (its last sub-sample) stops. In addition, for sub-sample n (n=1, 2, 3) of the PMD sample, the times at which the first and last volume elements enter the probe window are denoted as $t_{o,n}$ and $t_{f,n}$, respectively. Finally, it is assumed that all flushing is done at the same flush rate Q (volume/time). Using this convention, the details of each sub-sample are as follows:

Sub-sample 1, which is initially pumped through the probe window without resting, corresponds to the residual dialysate that is left in the outlet tubing after flushing out the previous sample. For this portion, the mass collected is $M_1$ and the volume $V_1$ is the volume of the outlet tubing. The times at which the first and last volume elements of the sub-sample enter the probe window, $t_{o,1}$ and $t_{f,1}$, and the exposure time for each volume element $\Delta t_1$ are $$t_{o,1}=t^0-(t_Q+V_1/Q) \quad t_{f,1}=t^0-V_1/Q \quad \Delta t_1=t_Q \quad (64)$$

Sub-sample 2, which follows the first one, is pumped into the probe window, allowed to occupy the window at rest for a specified resting time tR, and then flushed out by sub-sample 3. For this portion, the mass collected is M2 and the volume V2=VW (the probe window volume). The time $t_{f,2}$ corresponds to the time when the flushing of the previous sample stops. The times at which the first and last volume elements of the sub-sample enter the probe window, and the exposure time for each volume element are $$t_{o,2}=t^0-t_Q \quad t_{f,2}=t^0 \quad \Delta t_2=t_R+t_Q \quad (65)$$

Sub-sample 3 is the final portion, and is used to flush the probe without resting to facilitate a more complete collection of the pulsed portion. For this portion, the mass collected is $M_3$ and the volume is $V_3=V_S-V_1-V_2$. The times at which the first and last volume elements of the sub-sample enter the probe window, and the exposure time for each volume element are $$t_{o,3}=t^0+t_R \quad t_{f,3}=t^0t_S-(t_Q+V_1/Q)\Delta t_3=t_Q \quad (66)$$

The total mass of drug in the PMD sample is $M=M_1+M_2+M_3$, and the total sample volume is $V_S=V_1+V_2+V_3$. (It should be noted that the total time to collect the sample, denoted by $t_S$, is not the same as the sum of the exposure times.)

Mass Accumulated in a PMD Sample when the Donor Concentration is Constant (Static)

When the donor concentration is constant, Equation (62) becomes $$\frac{dm}{dt} = \frac{dC}{dt}dV = \gamma_1 C_D \exp(-\gamma_1 t_E) Q dt'$$

Performing the integrations in Equation (63) gives the mass in the sub-sample n as $$M_n = C_D V_n [1-\exp(-\gamma_1 \Delta t_n)]$$

where the sub-sample volume $V_n$ is given as $$V_n = Q[(t^0+t_{f,n})-(t^0+t_{o,n})] = Q(t_{f,n}-t_{o,n})$$

Summing the mass over the three sub-samples gives the mass in the total PMD sample as $$M = \sum_{n=1}^{3} V_n C_D [1-\exp(-\gamma_1 \Delta t_n)] \quad (67)$$

Experimentally, the mass in the in the PMD sample is found from $$M=V_S C_S \quad (68)$$

where $C_S$ is the concentration of drug in the PMD sample. Thus, the fraction recovered $F_R$ for the PMD sample is given by $$F_R = \frac{C_S}{C_D} = \frac{1}{V_S} \sum_{n=1}^{3} V_n [1-\exp(-\gamma_1 \Delta t_n)] \quad (69)$$

Knowing the sub-sample volumes and the $F_R$ (which is found from the slope of a $C_S$ vs. $C_D$ plot), Equation (69) can be used to obtain $\gamma_1$.

Mass Accumulated in a PMD Sample when the Donor Concentration is Changing (Dynamic)

When the donor concentration is changing, $C_D$ must now be represented as a function of time. In practice, two factors influence how $C_D$ is represented. First, it should be possible to integrate and differentiate the function (analytically or numerically). Second, the function should be of a form that is suited to represent the anticipated experimental data (usually based on a physical model).

In this work, two systems were studied—a simulated first order decline in donor concentration, and the protein binding. For both cases, the (free) drug concentration in the donor over the entire experiment was modeled as a function of time using a bi-exponential function plus a constant, of the form $$C_D = a_1 \exp(-b_1 t) + a_2 \exp(-b_2 t) + a_3 \quad (70)$$

(This choice of function was motivated in part by the protein binding kinetics model presented below. It is also appropriate for the first order experiments, with $a_2$ and $a_3 \to 0$.) Here, one set of fitting parameters $(a_j, b_j)$ is used to characterize the time behavior of $C_D$ over the entire time of the experiment. It is important to note that these parameters reflect processes affecting the donor concentration, and are independent of the probe as well. In addition, the fitting parameters do not have to have physical significance, but are only required to fit the data numerically. Equation (70) can be written more compactly as $$C_D = \sum_{j=1}^{3} a_j \exp(-b_j t) \quad (71)$$

(The constant term is achieved by letting $b_3 \to 0$.) With this choice, Equation (62) gives $$\frac{dm}{dt} = \gamma_1 Q \exp[-\gamma t_E] \sum_{j=1}^{3} a_j \exp[-b_j(t'+t_E)]dt'$$

If all PMD samples are collected using the same procedure, then for a given n, $\Delta t_n$ is the same for all i. (In other words, $\Delta t_1$ is the same for all PMD samples, etc.), and Equation (63) gives the mass in sub-sample n of the i$^{th}$ PMD sample as $$M_n = \sum_{j=1}^{3} \left(\frac{Q\gamma_1 a_j}{b_j(b_j+\gamma_1)}\right) \times \quad (72)$$
$$\{1-\exp[-(b_j+\gamma_1)\Delta t_n]\} \times \{\exp[-bt_{0,n}] - \exp[-bt_{0,f}]\}$$

The total mass in the PMD sample is given by $$M=M_1+M_2+M_3 \quad (73)$$

and the overall concentration in the PMD sample is given by $$C_S = \frac{M}{V_S} \quad (74)$$

Once the PMD sample concentration $C_S$ is obtained, it is possible to plot the donor concentration at any time within the sampling interval. However, it is most convenient to calculate $C_D$ at the start time of the PMD sample $t^0$. For comparison with the static calibrations, it is possible to define another fractional recovery, denoted as $F_R^0$ as the ratio of the $C_S$ to the donor concentration at the start of the interval, or $$F_R^0 = \frac{C_S}{C_D(t^0)} \quad (75)$$

As mentioned above, the time dependence of $C_D$ over the time of the experiment is characterized by the set of fitting parameters ($a_j$, $b_j$). The flush rate Q is selected before the experiment, the sub-sample volumes are known (thus allowing the time parameters to be calculated using Equations (64)-(66)), and $\gamma_1$ can be determined experimentally from static data using Equation (69). Thus, if enough PMD samples are collected, the values of $a_j$ and $b_j$, can be found by a nonlinear regression analysis, in which Equations (72)-(74) are fit to the PMD data.

It should be noted that, when the donor concentration is constant, Equations (72)-(74) give the same result as Equation (67), and $F_R^0 = F_R$. Mathematically, this is done by requiring that $\Sigma a_i = C_D$, and setting the $b_i = 0$ (which is done by first expanding the exponentials and then taking the limit as $b \rightarrow 0$.)

Numerical Procedure

The implementation of the above equations is described below and illustrated in the Examples. Fitting functions for the data should be carefully chosen, with the following guidelines in mind. First, the fitting function should be smooth and differentiable, and capture the essential features of the physical data (i.e., maxima/minima and the asymptotic behavior). In addition, if a mathematical model is being used to analyze the experimental data, the fitting function must have at least as many degrees of freedom (i.e., fitting parameters $a_i$ and $b_j$) as the basic physical equations. Further, good fitting practices should be followed (more data points than fitting parameters, sufficient number of points to characterize any curvatures, etc.). The procedure is as follows:

For the probe or combination of probes being used, the probe or set of probes should be calibrated for the static $F_R$ (constant concentration in the medium outside the probe or probes) for a given resting time, and using a number of different sample volumes.

From the static $F_R$, determine the value of $\gamma_1$ for the probe or combination of probes using Equation (69). (Alternatively, $\gamma_1$ can be obtained from $F_R$ vs. $t_R$ data, as described below.) However, when the donor concentration is changing, it is preferable to use this method because it reflects the behavior of a particular probe or set of probes in this context.)

From the experiments in which the donor concentration is changing, fit the PMD data in terms with the empirical function given by Equation (70) or (71) using Equations (72)-(74).

Take the plot times as the beginning of each PMD sample (i.e., when the flushing from the previous sample has stopped), and calculate the corresponding concentration in the donor using the $F_R^0$ given by Equation (75).

EXAMPLE 1

Determination of $F_{RQ}$ when the Donor Medium is Outside the Probe and the Donor Concentration is Constant It is possible to measure the $F_{RQ}$ directly using CFMD data. Alternatively, it is possible to obtain this parameter using PMD data. In this application, the donor is outside the probe, and its concentration is taken as constant (so the $F_{RQ}$ is well defined).

An example of a method that uses PMD to determine $F_{RQ}$ is as follows:
a) Immerse a probe in a solution (medium outside the probe) containing a known concentration of drug. The volume of the external solution should be large enough (at least ~25 mL) so drug transfer to the dialysate will not change the external medium concentration.
b) Pump fresh dialysate (i.e., containing no drug) into the probe window. The dialysate should be the same liquid as the external medium. It is preferable that the flow rate Q be relatively high (at least ~100 µL/min), so that $F_{RQ}$ is much smaller than 1.
c) Allow the dialysate to occupy the probe at rest for a known time $t_R$.
d) Flush and collect a known sample volume $V_S$ of the dialysate at the same flow rate Q. $V_S$ must be sufficient to collect all of the dialysate that was at rest in the window.
e) Perform an appropriate assay (HPLC, etc.) to determine the concentration and amount of drug in the dialysate sample, and calculate the $F_R$ from Equation (1).
f) Repeat steps b) through e) using the same sample volume and flow rate, but for at least one (preferably at least four) different resting times.
g) Fit a plot of the $F_R$ vs. $t_R$ to the empirical function given by Equation (26).
h) Set $t_R = 0$ and calculate $F_{RQ}$ from Equation (27).

EXAMPLE 2

Determination of $R_{FQ}$ when the Donor Medium is Inside the Probe and Concentration Outside the Probe is Zero Here, $R_{FQ}$ will be obtained using PMD data. In this application, the dialysate serves as the donor and the medium surrounding the probe is the receiver with a constant concentration. (In other words, the mass lost by the dialysate does not significantly change the receiver concentration.)

An example of a method that uses PMD to determine $R_{FQ}$ is as follows:
a) Immerse a probe in a solution (medium outside the probe) containing a known concentration of drug. The volume of the external solution should be large enough (at least ~25 mL) so drug transfer to the dialysate will not change the external medium concentration.
b) Pump dialysate containing a known concentration of drug $C_0$ into the probe window. The dialysate should be the same liquid as the external medium. It is preferable that the flow rate Q be relatively high (at least ~100 µL/min), so that $R_{FQ}$ is much smaller than 1.
c) Allow the dialysate to occupy the probe at rest for a known time $t_R$.

d) Flush and collect a known sample volume $V_S$ of the dialysate at the same flow rate Q. $V_S$ must be sufficient to collect all of the dialysate that was at rest in the window.
e) Perform an appropriate assay (HPLC, etc.) to determine the concentration and amount of drug in the dialysate sample, and calculate the $R_F$ from Equation (2).
f) Repeat steps b) through e) using the same sample volume and flow rate, but for at least one (preferably at least four) different resting times.
g) Fit a plot of the $R_F$ vs. $t_R$ to the empirical function given by Equation (54).
h) Set $t_R=0$ and calculate $R_{FQ}$ from Equation (55).

EXAMPLE 3

Determination of the Probe Window Volume

Measuring the window volume in this way is preferred since done in the context of the way the probe would actually be used, and also inherently takes into account any irregularities in the probe geometry which would give somewhat erroneous results using other methods, such as optical measurements.

An example of a method that uses PMD to determine $V_W$ is as follows:
a) Immerse a probe in a solution (medium outside the probe) containing a known concentration of drug. The volume of the external solution should be large enough (at least ~25 mL) so drug transfer to the dialysate will not change the external medium concentration.
b) Pump fresh dialysate (i.e., containing no drug) into the probe window. The dialysate should be the same liquid as the external medium. It is preferable that the flow rate Q be relatively high (at least ~100 μL/min), so that $F_{RQ}$ is much smaller than 1.
c) Allow the dialysate to occupy the probe at rest for a known resting time $t_R$. It is preferred that the resting time be long enough (typically ~3-10 minutes) so the $F_{RF} \approx 1$.
d) Flush and collect a known sample volume $V_S$ of the dialysate at the same flow rate Q. $V_S$ must be sufficient to collect all of the dialysate that was at rest in the window.
e) Perform an appropriate assay (HPLC, etc.) to determine the concentration and amount of drug in the dialysate sample, and calculate the $F_R$ from Equation (1).
f) Repeat steps b) through e) using the same resting time and flow rate, but for at least one (preferably at least three) different sample volumes.
g) Plot $F_R$ vs. $1/V_S$, which will give a straight line (e.g., FIG. 7), and determine the slope and intercept.
h) From Equation (24), the intercept will equal the $F_{RQ}$ and the slope will equal $V_W(1-F_{RQ})$ for long enough resting time. Thus, $$V_W = \frac{\text{slope}}{(1-F_{RQ})} = \frac{\text{slope}}{(1-\text{intercept})}.$$

EXAMPLE 4

Determination of $\gamma_1$

Measuring the value of $\gamma_1$ in this way is one of the preferred ways because it does not require a knowledge of $V_W$. However, knowledge of $V_W$ is still desirable because it can be used to improve the accuracy of the method.

An example of a method that uses PMD to determine $\gamma_1$ is as follows:
a) Immerse a probe in a solution (medium outside the probe) containing a known concentration of drug. The volume of the external solution should be large enough (at least ~25 mL) so drug transfer to the dialysate will not change the external medium concentration.
b) Pump fresh dialysate (i.e., containing no drug) into the probe window. The dialysate should be the same liquid as the external medium. It is preferable that the flow rate Q be relatively high (at least ~100 μL/min), so that $F_{RQ}$ is much smaller than 1.
c) Allow the dialysate to occupy the probe at rest for a known time $t_R$.
d) Flush and collect a known sample volume $V_S$ of the dialysate at the same flow rate Q. $V_S$ must be sufficient to collect all of the dialysate that was at rest in the window.
e) Perform an appropriate assay (HPLC, etc.) to determine the concentration and amount of drug in the dialysate sample, and calculate the $F_R$ from Equation (1).
f) Repeat steps b) through e) using the same sample volume and flow rate, but for at least one (preferably at least four) different resting times.
g) Determine the $F_{RQ}$ from CFMD data or the method of Example 1.
h) Using the values of the sample volume and the window volume (such as determined from Example 1), calculate the $F_{RP}$ for each resting time from Equation (24).
i) Plot ln $(1-F_{RP})$ vs. $t_R$ or $t_P$. This plot will give a straight line (e.g., FIG. 7) with a slope of $\gamma_1$.

EXAMPLE 5

Determination of $\gamma_1$

Measuring the value of $\gamma_1$ in this way is one of the preferred ways because it does not require a knowledge of $F_{RQ}$. It also does not require knowledge of $V_W$, but knowing of $V_W$ is desirable because it can be used to improve the accuracy of the method.

An example of a method that uses PMD to determine $\gamma_1$ is as follows:
a) Immerse a probe in a solution (medium outside the probe) containing a known concentration of drug. The volume of the external solution should be large enough (at least ~25 mL) so drug transfer to the dialysate will not change the external medium concentration.
b) Pump fresh dialysate (i.e., containing no drug) into the probe window. The dialysate should be the same liquid as the external medium. It is preferable that the flow rate Q be relatively high (at least ~100 μL/min), so that $F_{RQ}$ is much smaller than 1.
c) Allow the dialysate to occupy the probe at rest for a known time $t_R$.
d) Flush and collect a known sample volume $V_S$ of the dialysate at the same flow rate Q. $V_S$ must be sufficient to collect all of the dialysate that was at rest in the window.
e) Perform an appropriate assay (HPLC, etc.) to determine the concentration and amount of drug in the dialysate sample, and calculate the $F_R$ from Equation (1).
f) Repeat steps b) through e) using the same sample volume and flow rate, but for at least one (preferably at least four) different resting times.
g) Fit a plot of the $F_R$ vs. $t_R$ to the empirical function given by Equation (26).
h) Take the derivative of the fitted equation to find $dF_R/dt_R$ as a function of $t_R$.

i) Plot ln $(dF_R/dt_R)$ vs. $t_R$, as prescribed by Equation (47). This plot will give a straight line (e.g., FIG. 7xxxx) with a slope of $\gamma_1$. The accuracy can be improved if the plot is made subject to the constraint that the intercept, given by Equation (48), is consistent with the value of $V_W$ found independently using the method of Example 1, and value of $\gamma_1$ found from the slope. (This would be done by an iterative procedure.)

EXAMPLE 6

Determination of the Probe Window Wall Permeability Coefficient: Drug Outside the Probe The permeability P of the probe window wall is defined at steady state by Equation (5), and measuring the rate at which a drug crosses the membrane will allow P to be determined. A simple method using PMD is described below, using a setup in which a drug that is initially in the external medium crosses the probe wall membrane and transfers into the dialysate. (It is also possible to determine the permeability using a setup in which the drug is initially in the dialysate, and measuring the rate at which it transfers into the external medium.)
a) Make a solution containing a known concentration of drug (typically in water or a buffer), and use it as the external medium. The volume of the external medium should be large enough (typically at least ~25 mL) so that the drug transferred to the dialysate will not significantly change the external medium concentration $C_D$.
b) Use the same medium that initially contains no drug as the dialysate. Immerse the probe into the external medium.
c) At a high flow rate Q (at least 100 µL/min), pump the dialysate into the probe.
d) Allow the dialysate to occupy the probe for a known resting time $t_R$.
e) Flush and collect a known sample volume $V_S$ of the dialysate at the same flow rate Q. It is preferred that $V_S$ is sufficient to collect all of the dialysate that was at rest in the window.
f) Perform an appropriate assay (HPLC, etc.) to determine the amount of drug in the dialysate sample.
g) Repeat steps c) through f) using the same flow rate and sample volume, but for at least one (preferably at least three) different resting times. It is preferred that at least one or two of the resting times be short, typically in the range of ~2-5 times the transit time $t_Q$, defined in Equation (13).
h) Plot the amount of drug in the dialysate sample vs. the resting time. The slope is dM/dt.
i) Determine the slope using points corresponding to small values of $t_R$. (This corresponds to accumulating only small amounts of drug in the dialysate and allows the approximation to be made that the concentration in the dialysate is much smaller than the concentration $C_D$ in the external medium, so Equation (38) can be used.)
j) Determine the area of the probe window (from its length and radius), and calculate the permeability using $$P = \frac{1}{AC_D}\frac{dM}{dt}.$$

EXAMPLE 7

Determination of the Probe Window Wall Permeability Coefficient: Drug Inside the Probe The permeability P of the probe window wall is defined at steady state by Equation (5), and measuring the rate at which a drug crosses the membrane will allow P to be determined. A simple method using PMD is described below, using a setup in which a drug that is initially in the dialysate crosses the probe wall membrane and transfers into an external medium. (It is also possible to determine the permeability using a setup in which the drug is initially in the external medium, and measuring the rate at which it transfers into the dialysate.)
a) Make a solution containing a known concentration of drug (typically in water), and use it as the dialysate. The volume of the external medium should be large enough (typically at least 25 mL) so that the drug transferred from the dialysate will not significantly change the external medium concentration.
b) Immerse the probe in a volume of the same liquid used in the dialysate that initially contains no drug. The volume of liquid outside of the probe should be large enough (typically at least ~25 mL) so that the drug concentration in the external medium is always negligible compared to the dialysate drug concentration. This allows the approximation $C_D - C_R = C_D$ in Equation (5), where $C_D$ represents the dialysate drug concentration.
c) At a high flow rate Q (at least ~100 µL/min), pump the dialysate into the probe.
d) Allow the dialysate to occupy the probe for a known resting time $t_R$.
e) Flush and collect a known sample volume $V_S$ of the dialysate at the same flow rate Q. It is preferred that $V_S$ is sufficient to collect all of the dialysate that was at rest in the window.
f) Perform an appropriate assay (HPLC, etc.) to determine the amount of drug left in the dialysate sample. Knowing the initial concentration and amount in the sample volume, calculate the amount of drug that was lost from the dialysate into the external medium.
g) Repeat steps c) through f) using the same flow rate and sample volume, but for at least one (preferably at least three) different resting times. It is preferred that at least one or two of the resting times be short, typically in the range of 2-5 times the transit time $t_Q$, defined in Equation (13).
h) Plot the amount lost from the sample vs. the resting time. The slope is dM/dt.
i) Determine the slope using points corresponding to small values of $t_R$. (This corresponds to losing only small amounts of drug from the dialysate and allows the approximation be made that $C_D$ is constant, so Equation (38) can be used.)
j) Determine the area of the probe window (from its length and radius), and calculate the permeability using $$P = -\frac{1}{AC_D}\frac{dM}{dt}.$$

EXAMPLE 8

Determination of the Window Wall Permeability Coefficient: Drug Outside the Probe An alternative method for determining P is based on transferring the drug from the external medium into the dialysate. A simple example is described below.
a) Immerse the probe in a solution (medium outside the probe) containing a known concentration of the drug. The volume of the external solution should be large enough (at least ~25 mL) so drug transfer to the dialysate will not change the external medium concentration.

b) At a high flow rate Q (at least ~100 μL/min), pump the dialysate through the probe continuously (i.e., CFMD) and collect a relatively large sample volume (typically 20-50 μL).

c) Perform an appropriate assay (HPLC, etc.) to determine the concentration and amount of drug in the dialysate sample. Calculate the $F_{RQ}$ from Equation (1)

d) At the same flow rate Q, pump the dialysate into the probe.

e) Allow the dialysate to occupy the probe for a known resting time $t_R$.

f) Flush and collect a known sample volume $V_S$ of the dialysate at the same flow rate Q. It is preferred that $V_S$ be sufficient to collect all of the dialysate that was at rest in the window.

i) Perform an appropriate assay (HPLC, etc.) to determine the concentration and amount of drug in the dialysate sample. Calculate the $F_R$ from Equation (1) and $F_{RP}$ from Equation (24), using the $F_{RQ}$ determined in steps d) and e).

g) Repeat steps f) through j) using the same flow rate and sample volume, but for at least one (preferably at least three) different resting times.

h) Plot ln (1−$F_{RP}$) vs. $t_P$, which will give a straight line according to Equation (31). The slope of the line will equal −$\gamma_1$.

i) Determine the window volume, as described in Example 3.

j) Calculate the permeability P from Equation (40).

EXAMPLE 9

Determination of D and λ

The parameter λ characterizes the transfer across the probe window and how that transfer affects the concentration of the agent in the dialysate. Preferably, λ is 0-10, more preferably 0-3, still more preferably <0.3.

An example method to determine the parameter λ for a probe using PMD is as follows:

a) Make a solution containing a known concentration of a drug in a liquid, and the external donor medium. The diffusion coefficient does not need to be known.

b) Follow the steps outlined in Example 1 to obtain the window volume $V_W$. From that value, and the length of the probe, obtain the probe radius a.

c) Follow steps b) through i) in the method to determine the permeability coefficient P for the probe (Example 2 or 3).

d) Once P has been determined, calculate $\beta_1$ from Equation (43) (using the value of $\gamma_1$ obtained from Example 2 or 3 while getting P.

e) From $\beta_1$, calculate D from Equation (42).

f) From $\beta_1$, calculate λ from Equation (9) or Equation (41)

EXAMPLE 10

Determination of λ

The parameter λ characterizes the transfer across the probe window and how that transfer affects the concentration of the agent in the dialysate. Preferably, λ is 0-10, more preferably 0-3, still more preferably <0.3.

An example method to determine the parameter λ for a probe using PMD is as follows:

a) Make a solution containing a known concentration of reference drug in a liquid, and use it as the dialysate. The diffusion coefficient of the reference drug in the dialysate must be known independently of this method (i.e., from the literature or measured in some other experiment).

b) Follow steps b) through i) in the method to determine the permeability coefficient P for the probe (Example 2 or 3).

c) Once P has been determined, calculate λ using Equation (9).

EXAMPLE 11

Determination of Diffusion Coefficient

If the probe has been characterized so that $V_W$ and λ are known, it is possible to determine the diffusion coefficient of any drug in the dialysate. A method of determining the diffusion coefficient of drugs in the dialysate is as follows.

a) Determine the probe window volume $V_W$ (for instance, using the procedure described above). Any drug can be used.

b) Using a reference drug, determine the value of λ (for instance, using the procedures described above).

c) Immerse the probe in a solution (medium outside the probe) containing a known concentration of the drug for which D is to be determined. The volume of the external solution should be large enough (at least ~25 mL) so drug transfer to the dialysate will not change the external medium concentration.

d) At a high flow rate Q (at least ~100 μL/min), pump the dialysate through the probe continuously (i.e., CFMD) and collect a relatively large sample volume (typically ~20-50 μL).

e) Perform an appropriate assay (HPLC, etc.) to determine the concentration and amount of drug in the dialysate sample. Calculate the $F_{RQ}$ from Equation (1)

f) At a high flow rate Q (same one used for CFMD above), pump the dialysate into the probe.

g) Allow the dialysate to occupy the probe for a known resting time $t_R$.

h) Flush and collect a known sample volume $V_S$ of the dialysate at the same flow rate Q. It is preferred that $V_S$ is sufficient to collect all of the dialysate that was at rest in the window.

j) Perform an appropriate assay (HPLC, etc.) to determine the concentration and amount of drug in the dialysate sample. Calculate the $F_R$ from Equation (1) and $F_{RP}$ from Equation (24), using the $F_{RQ}$ determined in steps d) and e).

i) Repeat steps f) through j) using the same flow rate and sample volume, but for at least one (preferably at least three) different resting times.

j) Plot ln (1−$F_{RP}$) vs. $t_P$, which will give a straight line according to Equation (31). The slope of the line will equal −$\gamma_1$.

k) Using the value of λ for the probe, calculate $\beta_1$ from Equation (33), then calculate the diffusion coefficient D using Equation (31).

EXAMPLE 12

General Description of PMD for Uptake into Dialysate

The PMD method was tested using methazolamide (Sigma Chemical, St. Louis, Mo.) as the test drug in a variety of in vitro experiments.

Microdialysis probes were constructed as follows. Hollow fibers made of reconstituted cellulose (Spectrum Laboratory, Brunswick, N.J.), with a molecular cut-off of ~18,000 Daltons (18 KD) were used as the dialysis membrane. The inner radius of the dialysis membrane tube was ~100 μm and the thickness of the membrane wall was ~8 µm. A segment of polyimide tubing (MicroLumen, Tampa, Fla.) with an outer radius of ~83 µm was connected to each end of the dialysis membrane and glued to it by cyanoacrylate glue, leaving a probe window of ~10 cm length. (It will be understood by those skilled in the art that a straight probe, comprising a straight, needle-type probe comprising a highly permeable tubular membrane concentrically positioned within an impermeable tube (such as those readily available from CMA Microdialysis AB, North Chelmsford, Mass.) could optionally also be used.) One segment (7 cm length) was then glued to a 15 cm Tygon® tube with a inner diameter of ~100 µm, which was connected to a syringe pump and served as an inlet tubing. The other segment (10 cm length) was used to collect the samples. A schematic diagram of such a probe is shown in FIG. 1. A Harvard Model PHD2000 programmable syringe pump (Harvard Apparatus, Holliston, Mass.) was used to pump 0.005N NaOH dialysate through the probe. A jacketed beaker with a magnetic stirrer was used as the in vitro donor compartment. Different concentrations of methazolamide (MTZ) solution in 0.005N NaOH (50 mL volume) were used as the donor medium. The dialysis membrane part of the probe was immersed in the donor medium and held stationary with a clamp. The MTZ solution was stirred continuously to keep a constant concentration at the fluid-membrane boundary. All studies were performed at 37° C. The outer tubing (10 cm length) was used to collect the dialysate into 0.25 mL pre-chilled plastic micro-centrifuge tubes. The samples were analyzed immediately by high-pressure liquid chromatography (HPLC). (Preliminary studies found no evidence of nonspecific binding or adsorption of MTZ to the sampling tubes.)

MTZ was analyzed by HPLC with UV detection, according to the method described in *J. Pharmocokin. Biopharm.*, 27(1): 45-66 (1999). The HPLC system consisted of a Shimadzu LC-10AD constant flow pump and SPD-10VA ultraviolet detector (Shimadzu, Piscataway, N.J.), and a column. Output from the detector was processed on a personal computer using TC4 Turbochrom HPLC software (Perkin-Elmer, Shelton, Conn.). Separation was accomplished with a µBondapak 300 mm×3.9 mm C18, column (Waters Corporation, Milford, Mass.). The mobile phase consisted of 20:80 acetonitrile:sodium acetate buffer (0.05 M, pH 4.0). The mobile phase flow rate was 1.5 mL/min and the detection wavelength was 290 nm. 10 µL samples were injected directly into the system using an auto-sampler. The method was validated in buffer and the coefficient of variation of the method was less than 2%. The HPLC standard curve was linear and followed the equation A=12.522C−87.465, where A is the absorbance and C is the MTZ concentration in µg/mL. The limit of quantitation was 25 ng/mL. All solvents used were HPLC grade.

A dialysate of 0.005N NaOH was perfused through microdialysis probes with different continuous flow rates (q=3, 5, 7, 10, 15, 20, 30, 40, 50, and 60 µL/min). The probes were immersed in an MTZ solution of known concentration. For each flow rate, samples were collected into 250 µl microtubes and analyzed by HPLC.

A dialysate of 0.005N NaOH was pumped into microdialysis probes, allowed to sit inside the probe for different resting times, and then flushed out. The sample volumes were chosen to exceed the volume occupied inside the microdialysis probe window (3.14 µL) plus the outer tubing (1.22 µL). Samples were collected for each resting time and analyzed by HPLC. Studies were performed varying the resting times, sample volumes, flow rates and probe lengths as follows:
$t_R$: 5, 7, 10, 15, 20, 25, 30, 40, 50, and 60 seconds
$V_S$: 5, 7, and 10 µL
Q: 50, 60, 80, 100, 150, and 200 µL/min
For each set of parameters, the pump was programmed to repeat the above procedures seven times. The last five repetitions were collected and combined to make up the sample to be assayed.

EXAMPLE 13

In Vitro Probe Calibration

PMD was performed for each probe window. The length of the window was measured, and it was subsequently immersed in MTZ solutions of various known concentrations. A sample volume of 5 µL and flow rate of 100 µL/min were selected. Samples were collected for each donor concentration and immediately analyzed by HPLC. Calibration studies were performed for various values of $t_R$ (10 and 15 seconds) and probe window lengths (nominally 5 and 10 cm, corresponding to window volumes of ~1.57 and 3.14 µL, respectively). All experiments were done in triplicate, and the calibration plots were constructed by plotting $C_S$ vs. $C_D$ according to Equation (1).

In addition to the initial probe calibration, subsequent "three-point" probe calibrations were done when appropriate to verify that the original calibration curves were still valid. These were done by repeating the above calibration procedure using three donor concentrations over the donor concentration range of interest and comparing the results with the original calibration.

In addition, it is possible to calibrate the microdialysis probe with respect to the volume of the probe window, $V_W$. This was done by choosing a constant resting time that is long enough (>5-10 minutes) so that $F_R$~1, keeping the flow rate constant, and varying the sample volume $V_S$. $V_W$ can be obtained from the slope of a plot of $F_R$ vs. $1/V_S$, according to Equation (24). Here, $F_{RQ}$ is the $F_R$ for continuous flow and was determined from CFMD experimental data.

EXAMPLE 14

In Vitro Cellular Drug Uptake Simulation

The medium outside the probe served as the donor in this case. A donor solution of MTZ was made with a known initial concentration $C_0$ and volume V. The MTZ concentration was reduced over time by adding fresh 0.005N NaOH solution (with no MTZ) to the solution at a constant flow rate q (volume/time) while stirring, and simultaneously removing the stirred solution at the same flow rate, both in a continuous manner. Using this setup, the volume of the solution remained constant and the MTZ concentration declined over time in a first order manner, according to the equation $$C = C_0 \exp(-kt)$$
$$k = \frac{q}{V}$$
$$t_{1/2} = \frac{0.693}{k}$$

where k is the first order rate constant, and $t_{1/2}$ is the concentration half life (time for the concentration to drop in half), which is constant for this setup. In this experiment, the $C_0$ was 54 mcg/mL, V was 50 mL, and q was 4.5 mL/min, which gave values of k=0.09 min$^{-1}$ and $t_{1/2}$=7.7 minutes. PMD was performed using a 10 cm probe with a sample volume of 5 flow rate of Q=100 μL/min, and resting time of 10 seconds. Samples (25 μL) were collected at the same times (0, 1, 2, 5, 10, 15, 20, 25, 30, 35, 40, 50 and 60 minutes) from both the donor solution and the dialysate, and immediately analyzed using HPLC. Three point probe calibrations were performed before each experiment.

EXAMPLE 15

Measuring a Rapid First Order Decline in the External Medium Concentration

The medium outside the probe served as the donor in this case. A donor solution of sodium warfarin in an aqueous buffer (pH=7.4) was made with a known initial concentration $C_0$ and volume V. The warfarin concentration was reduced over time by adding fresh buffer solution (with no warfarin) to the solution at a constant flow rate q (volume/time) while stirring, and simultaneously removing the stirred solution at the same flow rate, both in a continuous manner. Using this setup, the volume of the solution remained constant and the warfarin concentration declined over time in a first order manner, according to the equation $$C = C_0 \exp(-kt)$$
$$k = \frac{q}{V}$$
$$t_{1/2} = \frac{0.693}{k}$$

where k is the first order rate constant, and $t_{1/2}$ is the concentration half life (time for the concentration to drop in half), which is constant for this setup. In this experiment, the $C_0$ was 100 mcg/mL, V was 50 mL. Various flow rates q were used, including 135 mL/min (half life of 16 seconds) and 230 mL/min (half life of 9 seconds). PMD was performed using two 10 cm probes with a sample volume of 22 μL (11 μL per probe), flow rate of Q=165 μL/min, and resting time of 3 seconds. PMD samples (22 μL) were collected every 7 seconds for two minutes and immediately analyzed using HPLC. Three point probe calibrations were performed before each experiment.

The concentration in the donor was obtained as follows. From a static probe calibration at a resting time of 3 seconds, the value of $\gamma_1$ for the probe was obtained from Equation (69). Subsequently, PMD was performed and single samples (i.e., samples were not combined) were collected every 7 seconds using a resting time of 3 seconds. The empirical function given by Equation (70) was fit to the PMD data using Equations (72)-(74). From that fit, the plot times were taken as the beginning of each PMD sample and the corresponding donor concentrations were calculated using the $F_R^0$ given by Equation (75).

EXAMPLE 16

Charcoal MTZ Adsorption Kinetics Study

The medium outside the probe served as the donor in this case. A charcoal suspension was prepared at least 24 hours before use by adding 0.6 g of activated charcoal (Sigma Chemical, St. Louis, Mo.) to 100 mL of 0.6% Dextran Solution (Birkmeier et al., 1995). A donor solution of MTZ in 0.005N NaOH was made with an initial concentration of $C_0$=200 μg/mL and volume of 48 mL. A probe was immersed in the solution, and PMD was started before adding the charcoal using a dialysate that initially contained no MTZ. Samples were collected every 10 seconds, using a resting time of 8 seconds, a flow rate of 100 μL/min, and a sample volume of 5 μL. After collecting at least six samples, 2 mL of the charcoal suspension was quickly (in 1-2 seconds) mixed into 48 mL of stirred MTZ solution, giving a final volume of 50 mL. The time at which the charcoal was added was taken as the start time (t=0) for the binding experiment. Samples were collected during 10 second intervals, and the start times for the sampling intervals were 0, 0.2, 0.4, 0.7, 1, 2, 5, 10 and 30 minutes. The flow rate was 100 μL/min, the rest time was 8 seconds, and the sample volume was 5 μL. The samples were immediately analyzed using HPLC. The study was done at 37° C., and a three-point probe calibration was performed before and after each experiment. Direct sampling of the donor was also done at various times for comparison with the PMD data. The direct donor samples were immediately filtered to remove the activated charcoal and analyzed using HPLC.

EXAMPLE 17

Serum Bovine Albumin (BSA) Warfarin Protein Binding Kinetics Study

The medium outside the probe served as the donor in this case. A 4% (by weight) aqueous solution of bovine serum albumin (BSA) was prepared at least 2 hours before use. An aqueous donor solution of warfarin was prepared separately. Two probes were immersed in the solution, and PMD was done using both probes simultaneously. PMD was started before adding the BSA solution, using a dialysate that initially contained no warfarin. Samples were collected every 7 seconds, using a resting time of 3 seconds, a flow rate of 165 μL/min, and a sample volume of 11 μL per probe, giving a total sample volume of 22 μL. After collecting enough samples to eliminate any residual drug (typically at least 6 samples, as in this example), the BSA solution was quickly added to the warfarin solution and mixed (over 1-2 seconds), giving a nominal total warfarin concentration of 100 mcg/mL. The time at which the BSA was added was taken as the start time (t=0) for the binding experiment. Various amounts of BSA were used to give a range of protein concentrations ranging from 4 to 20 mg/mL. Simultaneously, PMD samples were collected every 7 seconds for three minutes, then at 5, 10, 15, 20, 30, 40, 50, and 60 minutes. Samples were immediately analyzed by HPLC. The study was done at 37° C., and a three point probe calibration was performed before each experiment.

EXAMPLE 18

Benzocaine Release from Self-Emulsifying Microemulsion Systems

The medium outside the probe served as the receiver in this case. Before the PMD experiments, various anhydrous liquid systems were made, to be used to release benzocaine. In all cases, two surfactants, Tween 20 and Cremophor EL (both from Sigma Chemical, St. Louis, Mo.), were blended in a 2:1 (weight:weight) ratio. Various amounts of peppermint oil were added (from 0 to 30% oil by weight) to make the anhydrous systems. Benzocaine (50 mg per gram of peppermint oil) was subsequently added to each system, and stirring was done until all benzocaine was dissolved and distributed within the oil and surfactant blend. These anhydrous systems were then diluted 1:25 in water, and used as the dialysate. A probe was immersed in 50 mL of water (which served as the receiver) that initially contained no drug. Since benzocaine is a weak base, various pH values were used, but the pH of the water and dialysate were the same in all cases. The dialysate (containing the microemulsions and acting as the donor) was pumped into the probe window, allowed to remain at rest for various resting times (5-100 seconds), pumped out and collected, and subsequently assayed for benzocaine content to determine the fraction of benzocaine lost as a function of the total time in the probe window. The flow rate Q was 100 µL/min and the sample volume was 5 µL. The study was done at 25° C., and a three point probe calibration was performed before each experiment.

EXAMPLE 19

Dissolution of Ibuprofen

The medium outside the probe served as the donor in this case. An aqueous solution of NaOH in water at pH=2.0 was prepared, and 50 mL of the solution was used as the external medium. The solution was maintained at 25° C. and stirred continuously using a magnetic stirrer. A microdialysis probe was place into the external medium 30 minutes before beginning the dissolution experiment. After 30 minutes, 100 mg of ibuprofen (which exceeded its solubility in water at that pH) was added to the medium. PMD was started before adding the ibuprofen, using a dialysate that initially contained no drug. Each PMD sample was taken by collecting five pulses with no waiting between pulses, discarding the first two and combining the next three. Each pulse was done using a resting time of 10 seconds, a flow rate of 100 µL/min, and a sample volume of 10 µL (per pulse), giving a total sample volume of 30 µL. Samples were collected beginning at 1, 2, 3, 5, 10, 20, 30, 45, 60, 90 and 120 minutes and immediately analyzed using HPLC. Since the dissolution rate was slow, the concentration in the donor was found using Equation (1). A three point probe calibration was performed before each experiment.

EXAMPLE 20

Enzyme Assay Procedure

The medium outside the probe serves as the donor in this case. An appropriate concentration of an enzyme is to be prepared before use. An aqueous donor solution of the drug is prepared separately. As an option, the concentration of the drug and/or enzyme can be adjusted to speed up or slow down the degradation rate of a drug in the presence of the enzyme. A microdialysis probe (or set of probes for fast reactions) is immersed in the drug solution, and PMD is started before adding the enzyme, using a dialysate that initially contains no drug. Samples are collected at appropriate times, using appropriate resting times, flow rates and sample volumes. The concentration in the donor for the free drug that has not yet undergone degradation is determined using Equation (1) or the method of Example 15. These choices will depend on whether the degradation occurs quickly (say, greater than 5% degradation per minute) or more slowly. (Compare Examples 14 and 17, for instance.) Three point calibrations are performed before and after each experiment.

RESULTS AND DISCUSSION

Sensitivity of PMD

In this study, a tubular probe was used. A schematic diagram is shown in FIG. 1, in which the permeable tubing (probe window) is represented by the broken lines and the impermeable tubing is represented by the heavy solid lines. The length of the probe window is L and the inner radius is a, and its volume is given by $V_W = \pi a^2 L$. The centerline (r=0) is represented by the dashed line.

The sensitivity of the PMD method was compared to that of the CFMD method by comparing the $F_R$ as a function of the sample collection rate. For CFMD, the sample collection rate is the volume of sample collected per time, and equals the continuous flow rate Q. For PMD, the sample collection rate is the sample volume divided by the time to collect the sample, and can thought of as an "average flow rate" $\langle Q \rangle$, given by $$\langle Q \rangle = \frac{V_S}{t_S} \qquad (76)$$

Here, $t_S$ is the time required to collect the entire sample, which is the sum of the time required to flush the sample volume plus the resting time, and is given by $$t_S = t_R + \frac{V_S}{Q} \qquad (77)$$

where Q is the flow rate used for flushing in the PMD experiment. For the PMD experiments, $\langle Q \rangle$ was changed by varying the resting time, while keeping the sample volume and flow rate for flushing constant ($V_S$=5 µL and Q=100 µL/min).

A comparison is shown in FIG. 2. There, the solid diamonds/solid line represents PMD data, and the open squares/dashed line represents CFMD data. In all cases, the temperature was 37° C., the probe window was 11.24 cm in length and had a nominal inner radius of 100µ, the flow rate for flushing 100 µL/min, and the sample volume $V_S$ was 5 µL. FIG. 2 shows that, at similar sample collection rates, the PMD and CFMD data displayed similar values of $F_R$, which decreased with increasing flow rates for both methods due to shorter exposure times.

The minimum measurable donor concentration was estimated by dividing the assay limit of quantitation (the lowest concentration that can be assayed by the HPLC with acceptable error) by the $F_R$. In this study, the HPLC limit for MTZ was ~25 ng/mL. For a 10 second resting time and 10 cm probe window, $F_R$~0.2 and the minimum measurable $C_D$ was ~125 ng/mL. For the same system and a 30 second $t_R$, $F_R$~0.6 and the minimum measurable $C_D$ was ~40 ng/mL. Thus, the sensitivity of the PMD method can be effectively adjusted by varying the resting time.

While PMD and CFMD show comparable sensitivity in determining drug concentrations, there are two important differences. First, if the concentration of drug in the medium outside the probe does not change, then all parts of a CFMD sample are identical. On the other hand, in the case of PMD, the continuous (flushed) portions are identical, but the pulsed (rested) portions are different if different resting times are used. In addition, while the pulsed portion is at rest, drug transport occurs by diffusion alone. Thus, a body of diffusion equations becomes available in PMD that allows the determination of properties such as diffusion coefficients, probe window permeabilities, etc. Since there is no passive diffusion phase in CFMD, these analyses are not applicable to that method.

The second difference occurs because the dialysate flow rate is constant and continuous in CFMD, so the sample is collected continuously over the sample interval (which is typically long). If the donor is outside the probe and the drug concentration changes significantly during the sampling interval, it is not feasible to assign an exact concentration to an exact time using CFMD. PMD is much better suited for this purpose, especially if the flushing is done using high flow rates, because almost all of the drug is accumulated in the sample during the resting time. If that resting time is short, PMD gives a "snapshot" of the system, and it is possible assign a donor concentration to a specific time.

Calibration Plots

To correlate the concentration between the sample and donor, calibration plots were made by plotting the $C_S$ vs. $C_D$. In CFMD, this is done in vitro by comparing dialysate sample concentrations with those of direct sampling of the donor, and the assumption is made that the relation between $C_S$ and $C_D$ does not change during the experiment. In this study, similar calibration plots were made using data obtained by PMD. It was observed that calibration plots were linear ($R^2 > 0.99$) in all cases. Some data is shown in FIGS. 3 and 4. FIG. 3 shows calibration curves for two different probes. There, the dashed line (triangles) represents data generated using a probe window of 11.24 cm length, and the solid line (circles) represents data generated using a probe window of 11.04 cm length. In both cases, the temperature was 37° C., the nominal inner radius of the probe window was 100μ, the resting time was 10 seconds, the sample volume was 5 μL and the flow rate was 100 μL/min. Both calibration curves were linear ($R^2 > 0.99$). The dashed line is described by the equation $C_S = 0.207 C_D + 21.53$, and the solid line is described by $C_S = 0.170 C_D + 30.17$. (The concentrations are in units of μg/mL.) Since the intercepts were close to the origin, the fraction recovered $F_R$ for a given probe was taken as being equal to the slope of the $C_S$ vs. $C_D$ plot. This shows that there may be some variation between microdialysis probes, so each must be calibrated individually.

The observed $F_R$ is affected by the exposure time of the sample, increasing with longer exposure. This is shown in FIG. 4, in which the solid line (diamonds) represents data generated using resting times of 10 seconds, and the dashed line (squares) represents data generated using resting times of 15 seconds. In both cases, the temperature was 37° C., the length of the probe window was 11.24 cm, the inner radius of the probe window was 100μ, the sample volume was 5 μL and the flow rate was 100 μL/min. Both calibration curves were linear ($R^2 > 0.99$). For the 10 second resting time data, the data fit the line $C_S = 0.207 C_D + 20.97$ ($F_R = 0.207$). For the 15 second resting $_{time}$ data, the data fit the line $C_S = 0.281\ C_D + 19.11$ ($F_R = 0.281$). The concentrations are in units of μg/mL. Thus, for the probes shown in FIG. 4, increasing the exposure time from 10 seconds to 20 seconds increases the $F_R$ from 0.207 to 0.281. This is because longer exposure of the dialysate to the donor solution allows more of the drug to diffuse into the dialysate. This effect is also illustrated in FIG. 5, which shows a plot of $F_R$ vs. $t_P$ for the 11.24 cm probe from FIG. 4. In FIG. 5, the squares represent experimental data points, and the line represents the best fit to the data using Equations (21)-(24).

The $F_R$ decreased with increasing sample volume and increased with the volume of the probe window in a manner that was also consistent with Equation (24). A plot of $F_R$ vs. $1/V_S$ is shown in FIG. 6. There, the temperature was 37° C., the length of the probe window was 5 cm, the nominal inner radius of the probe window was 100μ, and the flow rate was 100 μL/min. The sample volume was varied, and the solid line is the linear best fit curve through the data points. The line has a slope of 2.71 and an intercept of 0.06 ($R^2 > 0.99$), corresponding to $V_W = 2.9$ μL. This value of $V_W$ differs somewhat from the value calculated based on the manufacturer's data for the probe radius. (Using the nominal radius of 100μ, and measured window length of 5 cm gives a nominal window volume of 1.5 μL). Using optical microscopy, it was verified that the probe diameter was significantly larger the nominal value, but the accuracy of optical microscopy is still inferior to the procedure used here.) In addition, the intercept (0.06) is in agreement with the $F_R$ obtained from CFMD experiments using the same flow rate. This is to be expected because the intercept occurs when $1/V_S \rightarrow 0$, which physically corresponds to CFMD.

FIG. 7 shows a plot of $\ln(1 - F_{RP})$ vs. $t_P$, as given by Equation (30) or (35), which is linear as expected. MTZ was used as the reference drug, which has a value of $4 \times 10^{-6}$ cm$^2$/s at 37° C., and $F_{RP}$ was found from $F_R$ using Equation (24), using a window volume of 3.6 μL. The temperature was 37° C., the probe window length was 11.24 cm, the probe window inner radius was 100μ, the sample volume was 5 μL and the flow rate was 100 μL/min. The line is linear (slope=$-0.0187$ s$^{-1}$, intercept=$-0.007$, $R^2 > 0.99$). From these results, the permeability of the probe window wall was P=$9.4 \times 10^{-5}$ cm/s and λ=0.23, which was in the expected range for this probe.

Time Resolution and Simulated Uptake Studies

The ability to detect relatively rapid changes in the donor concentration can be an important consideration for systems in which the concentration changes rapidly, such as might occur with in vitro cellular uptake or binding studies. Since the CFMD method typically requires several minutes for sample collection, it is not possible to assign accurate times (either exact or to within short time intervals) to the dialysate sample concentrations. This is one of the primary reasons for inventing the PMD method, which can assign concentrations to short and specific time intervals, which correspond to the sampling interval time $t_S$ defined in Equation (77).

For systems in which the donor concentration is changing, plots of concentration (or some function of the concentration) vs. time are usually the preferred way to view or analyze the experimental data. For these PMD experiments, the concentration being is determined from the dialysate sample concentration, which can be used as is or used to calculate the concentration in the medium outside the probe using Equation (1) (depending on the experiment being done). The time t at which that concentration is plotted is taken as $$\text{Plot time } t = \begin{bmatrix} \text{time after the start of the experiment when} \\ \text{a particular } PMD \text{ sampling begins} \end{bmatrix} + \begin{bmatrix} \text{half the time required to} \\ \text{take the } PMD \text{ sample} \end{bmatrix}$$

which can be calculated as $$t = t_{plot} = t_{\substack{begin \\ sample}} + \frac{t_S}{2} \tag{78}$$

When the donor concentration changes rapidly, a more accurate procedure is used to determine the donor concentration and plot time. This is done using the analysis leading to Equations (72)-(75) and doing the nonlinear regressions to determine the fitting parameters used in an appropriate fitting function, such as that given by Equation (71). This should be used when the change in the donor concentration between the time an individual PMD sample is started and complete is significant. (For instance, more than 5% loss, although this could be greater or smaller, depending on the accuracy needed in an experiment. For protein binding experiment, an error greater than 5% would be undesirable, for example.)

As mentioned above, one of the features that makes PMD well suited for sampling changing concentrations is that the time during which the dialysate accumulates or loses a compound by diffusion is well defined, so specific concentrations can be assigned to specific times and/or time intervals. Another advantage is that the time interval $t_S$ can be very short (as short as four or five seconds), which is very important when sampling concentrations that change, but is not possible with other types of experimental setups. The ability to sample in short intervals occurs because the radii of the probes are very small, which has two important implications.

The diffusing molecules do not have to travel very far (relative to other methods) before a significant portion of the dialysate volume gains or loses molecules. Thus, in a given time interval, a larger fraction of the dialysate is affected by drug diffusion.

The surface/volume ratio of the probe is very large (relative to other methods). This is relevant because the rate at which molecules diffuse across the probe wall is proportional to its area, while the change in dialysate concentration is inversely proportional to its volume. Thus, in a given time interval, larger surface/volume ratios lead to larger concentration changes in the dialysate.

The combined effect is that PMD can measure concentrations and concentration changes (inside or outside the probe) by taking samples over short intervals $t_S$. This was tested in several experiments, as discussed below.

A first order uptake was simulated by adding 4.5 mL/min to 50 mL of stirred MTZ solution in NaOH, and simultaneously removing 4.5 mL/min of the mixture. This maintained a constant donor solution volume, but the MTZ concentration declined according to the equation $C=C_0 \exp(-kt)$. Based on the pump rates, the calculated value of the rate constant was $k=0.090$ min$^{-1}$ (half-life of 7.7 hours). FIG. 8 shows the results for that experiment using a temperature of 37° C., probe window length of 11.24 cm, nominal inner radius of the probe window of 100μ, sample volume of 5 μL, and the flow rate of 100 μL/min. The value found from direct sampling of the donor solution (dashed line) was $k=0.088$ min$^{-1}$, and the value found from the PMD data (solid line) was $k=0.089$ min$^{-1}$. The intercept from the direct sampling data=10.887 and the intercept from the PMD data=9.150. Theoretically, the difference between the intercepts of the ln C vs. t plots for the PMD and direct donor sampling data should be equal to ln $(F_R)$. From the data shown in FIG. 8, the intercepts for PMD and direct sampling-differ by −1.737, giving an $F_R$=0.176. This value is nearly identical to the of 0.178 obtained from the calibration plot for this PMD setup.

In the second experiment, a more rapid first order decline in donor concentration was brought about. This was done for the drug sodium warfarin in an aqueous buffer by adding fresh buffer to 50 mL of stirred warfarin solution at various flow rates and simultaneously removing the stirred mixture at the same flow rate. The temperature was 37° C., two probes were used simultaneously (window volume was 5 μL per probe), the sample volume was 22 μL (11 μL per probe), the resting time was 3 seconds and the flow rate was 165 μL/min. The same equations used for the MTZ experiment apply, but the pump rates ranged up to 230 mL/min. Based on the pump rates, the calculated values of the rate constant were as high as $k=0.077$ sec$^{-1}$. Donor concentrations calculated using PMD and the model leading to Equations (72)-(75) were in excellent agreement, using the fitting function given by Equation (71). Data for the 16 second half life experiments, in which the pumping rates were chosen to mimic a first order rate constant of $k=0.043$ sec$^{-1}$, are shown in FIG. 9. There, the open circles represent the PMD concentrations, the filled triangles represent the donor concentration plotted at appropriate times, as calculated from the PMD sample data. The solid line represents the theoretical value of the donor concentration that was calculated using the theoretical rate constant. It can be seen that the calculated and theoretical donor concentrations are in excellent agreement. Since the decline was designed to be first order, a plot of the natural log of the calculated (from PMD data) and theoretical donor concentrations from the first order rate constant) vs. time is shown in FIG. 10. There, the filled triangles represent the donor concentration plotted at appropriate times, as calculated from the PMD sample data. The solid line represents the theoretical value of the donor concentration that was calculated using the theoretical rate constant. FIG. 10 shows that the rate constant k for the calculated and theoretical donor concentrations are in excellent agreement ($k=0.044$ sec$^{-1}$ for the decline calculated from PMD data vs. $k=0.043$ sec$^{-1}$ for the theoretical value calculated from the pumping rates).

In a third experiment, activated charcoal was added to an MTZ solution and the donor concentrations were simultaneously sampled using PMD and direct donor sampling. In this system, the donor concentration dropped rapidly over the first minute, and declined slowly after that. The results are shown in FIG. 11 for the first five minutes of the experiment (after which time the concentrations did not change). In that experiment, the temperature was 37° C., the length of the probe window was 11.24 cm, the nominal inner radius was 100μ, the sample volume was 5 μL and the flow rate was 100 μL/min. In the figure, the diamonds represent data obtained using PMD, and the large open circles represent data obtained from direct donor sampling. The data obtained using PMD and direct donor sampling were in excellent agreement, and indicated that the free MTZ concentration fell from 5.4 to 2.8 μg/mL over the first minute after the addition of the activated charcoal. (It should be noted that direct donor samples taken before the first minute were very inconsistent. This is because adsorption was still going on while the charcoal and free drug were being separated.) In addition, the PMD method was able to generate six concentration measurements over the first minute. Thus, PMD was able to characterize the concentration vs. time profile, even during the first minute of the experiment (when the concentration declined by nearly 50%). As a rough check for consistency of the PMD data, the rate of change of $C_D$ was plotted as a function of time. This plot was smooth, continuous and the rate monotonically approached zero. (While this does not imply anything about the physical process that governs the adsorption kinetics, all of these characteristics should be expected from experimental data.)

In an analogous experiment using proteins, a solution of BSA (bovine serum albumin) was added to an aqueous solution of sodium warfarin in phosphate buffer, and the donor concentrations were sampled using PMD. The temperature was 37° C., the pH was 7.4, the concentration of the BSA solution before mixing with the warfarin solution was 40 mg/mL. After mixing the warfarin and BSA solutions, the total warfarin concentration was 102 mcg/mL (0.31 mM) and the total BSA concentration was 16 mg/mL. The results are shown in FIG. 12, in which the points represent the experimental warfarin concentrations and the solid line represents the best fit curve using a postulated binding model. It was seen that the donor warfarin concentration dropped rapidly over the first minute, and declined slowly after that, and reached equilibrium after a few minutes. The results are shown only for the first 90 seconds of the experiment, after which time the concentrations did not change. The PMD method was able to generate eight concentration measurements over the first minute and was able to characterize the concentration vs. time profile for the entire course of the binding process.

In a different experiment, the release of benzocaine from various microemulsion systems was studied. In these experiments, the donor liquid was the dialysate and the receiver was the medium outside of the probe. Thus, PMD was used to measure the amount of drug lost by the dialysate, and the fraction remaining $R_F$ was calculated. The microemulsion systems used here contained Tween 20:Cremophor EL:peppermint oil mixtures, which were diluted in water after mixing in a 1:25 weight ratio. For these systems, the release of the drug was relatively rapid (losing as much as 90% of the benzocaine when occupying the probe window for one minute). FIG. 13 shows the log of the fraction remaining vs. time for the release of benzocaine from a microemulsion at 25° C., in which the surfactant was a 2:1 (weight/weight) blend of Tween 20 plus Cremophor EL, and the surfactant: peppermint oil weight ratio was 90:10 (before adding water). The triangles represent the experimental data, the line represents the best fit line. (On the vertical axis, the notation $f_{rem}$, is used to denote the $R_F$, which is the fraction of the total drug loaded remaining in the dialysate.)

I claim:

1. A method for accurately determining the rate at which a diffusible agent interacts with an interactive agent, comprising:
   a) providing a probe comprising a section of relatively highly permeable membrane relative to any materials to which the membrane is attached for support and positioned between an inlet to a source of dialysate and an outlet to a receptacle, and through which membrane a diffusible agent is to be transferred;
   b) determining the value of $\gamma_1$ for the probe using a chosen sample volume, flow rate and resting time;
   c) putting said probe in contact with said medium in which is contained the agent to be transferred by diffusion;
   d) to said medium containing the agent that will transfer by diffusion, adding a second agent that will interact with the diffusible agent;
   e) perfusing a known quantity of a dialysate into the relatively highly permeable section of the probe at the same flow rate Q used to calculate $\gamma_1$;
   f) allowing said known quantity of dialysate to remain stationary for the same resting time $t_R$ used to calculate $\gamma_1$;
   g) flushing out said known quantity of dialysate with a single pulse to collect a sample of dialysate, of the same volume as that chosen in step (b), of a known volume $V_S$, dialysate into said receptacle at the same flow rate used in step (d), above;
   h) determining the concentration of said diffusible agent in said dialysate;
   i) repeating steps (e) through (h) with the same flow rate, sample volume, and resting time;
   j) determining the fractional recovery at the beginning of a sample interval by calculating $F_R^0$;
   k) calculating the concentration in the medium at the beginning of the sample interval as $C_D = C_S/F_R^0$.

2. A method of claim 1 in which the interactive agent at least partially binds with the diffusible agent.

3. A method of claim 1 in which the interactive agent at least partially adsorbs the diffusible agent.

4. A method of claim 1 in which the interactive agent at least partially forms a complex with the diffusible agent.

5. A method of claim 1 in which the interactive agent causes the diffusible agent to at least partially precipitate.

6. A method of claim 1 in which the interactive agent causes the diffusible agent to at least partially form an emulsion or suspension.

7. A method of claim 1 in which the interactive agent is an enzyme or catalyst, which will cause the diffusible agent to chemically degrade.

8. A method of claim 1 in which the interactive agent is a chemical that reacts with the diffusible agent to create a different chemical entity.

9. A method of claim 1 in which the interactive agent is the diffusible agent itself and causes itself to at least partially precipitate due to supersaturation.

\* \* \* \* \*